(12) United States Patent
Meyer et al.

(10) Patent No.: US 11,427,628 B2
(45) Date of Patent: Aug. 30, 2022

(54) ANTIBODY FRAMEWORKS

(71) Applicant: NUMAB THERAPEUTICS AG, Wädenswil (CH)

(72) Inventors: Sebastian Meyer, Eggenwil (CH); David Urech, Jona (CH)

(73) Assignee: NUMAB THERAPEUTICS AG, Wädenswil (CH)

( * ) Notice: Subject to any disclaimer, the term of this patent is extended or adjusted under 35 U.S.C. 154(b) by 166 days.

(21) Appl. No.: 16/156,036

(22) Filed: Oct. 10, 2018

(65) Prior Publication Data

US 2019/0119359 A1 Apr. 25, 2019

Related U.S. Application Data

(62) Division of application No. 14/900,550, filed as application No. PCT/EP2014/001730 on Jun. 26, 2014, now Pat. No. 10,174,102.

(30) Foreign Application Priority Data

Jun. 26, 2013 (EP) .................................... 13003264

(51) Int. Cl.
*C07K 16/00* (2006.01)
*C07K 16/24* (2006.01)
*C12N 15/10* (2006.01)
*G01N 33/531* (2006.01)

(52) U.S. Cl.
CPC ............ *C07K 16/00* (2013.01); *C07K 16/241* (2013.01); *C12N 15/1068* (2013.01); *G01N 33/531* (2013.01); *C07K 2317/24* (2013.01); *C07K 2317/565* (2013.01); *C07K 2317/567* (2013.01); *C07K 2317/622* (2013.01); *C07K 2317/94* (2013.01)

(58) Field of Classification Search
CPC .......... C07K 2317/24; C07K 2317/567; C07K 2317/94
USPC ...................................................... 424/135.1
See application file for complete search history.

(56) References Cited

U.S. PATENT DOCUMENTS

| 5,530,101 A * | 6/1996 | Queen ................. C07K 16/2866 530/387.3 |
| 10,174,102 B2 | 1/2019 | Meyer |
| 2020/0255533 A1 * | 8/2020 | Diem ................. C07K 16/2866 |

FOREIGN PATENT DOCUMENTS

| EP | 3 013 864 | 5/2016 |
| WO | 2009/155724 A2 | 12/2009 |
| WO | 2009155723 A2 | 12/2009 |
| WO | 2009155726 A2 | 12/2009 |
| WO | 2014206561 A8 | 12/2014 |
| WO | 2019/057787 A1 | 3/2019 |

OTHER PUBLICATIONS

Agparetal (MABS vol. 8, No. 7, 1302-1318 (2016)).*
Dondelinger et al (Frontiers in Immunol vol. 9: 1-15 (Oct. 16, 2018)).*
Forstora Search Report dated Oct. 7, 2014 in PCT/EP2014/001730 (5 pages).
Boras et al., "Generic Approach for the Generation of Stable Humanized Single-chain Fv Fragments from Rabbit Monoclonal Antibodies", J. Biol. Chem. Mar. 19, 2010; 285(12):9054-66. doi: 10.1074/jbc.M109.072876. Epub Jan. 7, 2010.
Carter et al., "Humanization of an anti-p185HER2 antibody for human cancer therapy", Proc. Natl. Acad. Sci. USA. May 15, 1992; 89(10):4285-9.
Ewert et al., "Stability improvement of antibodies for extracellular and intracellular applications: CDR grafting to stable frameworks and structure-based framework engineering", Methods Oct. 2004;34(2):184-99.
Abhinandan et al., "Analysis and improvements to Kabat and structurally correct numbering of antibody variable domains," Molecular Immunology, vol. 45, pp. 3832-3839 (2008).
Dufner et al., "Harnessing phase and ribosome display for antibody optimisation," TRENDS in Biotechnology, vol. 24, No. 11, pp. 523-529 (2006).
Egan et al., "Novel multispecific heterodimeric antibody format allowing modular assembly of variable domain fragments," MABS, vol. 9, No. 1, pp. 68-84 (2017).
Lederman et al., "A Single Amino Acid Substitution in a Common African Allele of the CD4 Molecule Ablates Binding of the Monoclonal Antibody, OKT4," Molecular Immunology, vol. 28, No. 11, pp. 1171-1181 (1991).
Lehmann et al., "Stability engineering of anti-EGFR scFv antibodies by rational design of a lambda-to-kappa swap of the VL framework using a structure-guided approach," mAbs vol. 7, No. 6, pp. 1058-1071 (Nov./Dec. 2015).
Li et al., "Beta-Endorphin omission analogs: Dissociation of immunoreactivity from other biological activities," Proc Natl. Acad. Sci. USA, vol. 77, No. 6, pp. 3211-3214 (Jun. 1980).
Ward et al., "Binding activities of a repertoire of single immunoglobulin variable domains secreted from *Eschericihia coli*," Nature, vol. 341, pp. 544-546 (1989).
Bowers et al, PNAS 2011 vol. 108 No. 51 pp. 20455-20460.
Ewert et al, JMB 2003 vol. 325 Issue 3 pp. 531-553.

* cited by examiner

*Primary Examiner* — Lynn A Bristol
(74) *Attorney, Agent, or Firm* — Prismatic Law Group, PLLC; Ron Kamis

(57) ABSTRACT

The present invention relates to antibody light chain framework regions I to III from Vκ and framework region IV from Vλ, with high stability and reduced aggregation propensity.

4 Claims, 5 Drawing Sheets

Specification includes a Sequence Listing.

Figure 2:

| | CDR L1 |
|---|---|
| AHo Hum cons VL-kI (Carter, 1992) | D I Q M T Q S P S S L S A S V G D R V T I T C . . . . . . . . . . . . . . . . W Y Q Q K P G |
| SEQ ID No 2 | D I Q M T Q S P S S L S A S V G D R V T I T C Q A S Q S . . . . . . . . I S D W L A W Y Q Q K P G |
| SEQ ID No 4 | E I V M T Q S P S T L S A S V G D R V I I T C Q A S Q S . . . . . . . . I S D W L A W Y Q Q K P G |
| SEQ ID No 6 | E I V M T Q S P S T L S A S V G D R V I I T C Q A S Q S . . . . . . . . I S D W L A W Y Q Q K P G |

| | CDR L2 |
|---|---|
| AHo Hum cons VL-kI (Carter, 1992) | K A P K L L I Y . . . . . . . . . . . . . G V P S R F S G S G S G . . T D F T L T I S S L Q P E |
| SEQ ID No 2 | K A P K L L I Y G A S . . . . . . . . R L A S G V P S R F S G S R S G . . T D F T L T I S S L Q P E |
| SEQ ID No 4 | K A P K L L I Y G A S . . . . . . . . R L A S G V P S R F S G S G S G . . A E F T L T I S S L Q P D |
| SEQ ID No 6 | K A P K L L I Y G A S . . . . . . . . R L A S G V P S R F S G S G S G . . A E F T L T I S S L Q P D |

| | CDR L3 |
|---|---|
| AHo Hum cons VL-kI (Carter, 1992) | D F A T Y Y C . . . . . . . . . . . . . . . . . . . . . F G Q G T K V E I K R |
| SEQ ID No 2 | D F A T Y Y C Q Q G W S D . . . . . . . . . . . . . . . S Y V D N L F G Q G T K V E I K R |
| SEQ ID No 4 | D F A T Y Y C Q Q G W S D . . . . . . . . . . . . . . . S Y V D N L F G Q G T K L T V L G |
| SEQ ID No 6 | D F A T Y Y C Q Q G W S D . . . . . . . . . . . . . . . S Y V D N L F G Q G T K V E I K R |

| | CDR H1 |
|---|---|
| AHo Hum cons VH3 (Carter, 1992) | E V Q L V E S . G G G L V Q P G G S L R L S C A A S . . . . . . . . . . . W V R Q A P G |
| SEQ ID No 3 | E V Q L V E S . G G G L V Q P G G S L R L S C A V S G F S L S . . . . . . S G A M S W V R Q A P G |
| SEQ ID No 5 | E V Q L V E S . G G G L V Q P G G S L R L S C T V S G F S L S . . . . . . S G A M S W V R Q A P G |

| | CDR H2 |
|---|---|
| AHo Hum cons VH3 (Carter, 1992) | K G L E W V S . . . . . . . . . . . . . . . R F T I S R D N S K N T L Y L Q M N S L R A E |
| SEQ ID No 3 | K G L E W I G V I I S S G A T . . . . Y Y A S W A K G R F T I S K D N S K N T V Y L Q M N S L R A E |
| SEQ ID No 5 | K G L E W V G V I I S S G A T . . . . Y Y A S W A K G R F T I S K D T S K N T V Y L Q M N S L R A E |

| | CDR H3 |
|---|---|
| AHo Hum cons VH3 (Carter, 1992) | D T A V Y Y C A . . . . . . . . . . . . . . . . . . . . W G Q G T L V T V S S |
| SEQ ID No 3 | D T A V Y Y C A R G G P D D S N . . . . . . . . . . . . . S M G T F D P W G Q G T L V T V S S |
| SEQ ID No 5 | D T A V Y Y C A R G G P D D S N . . . . . . . . . . . . . S M G T F D P W G Q G T L V T V S S |

Figure 4:
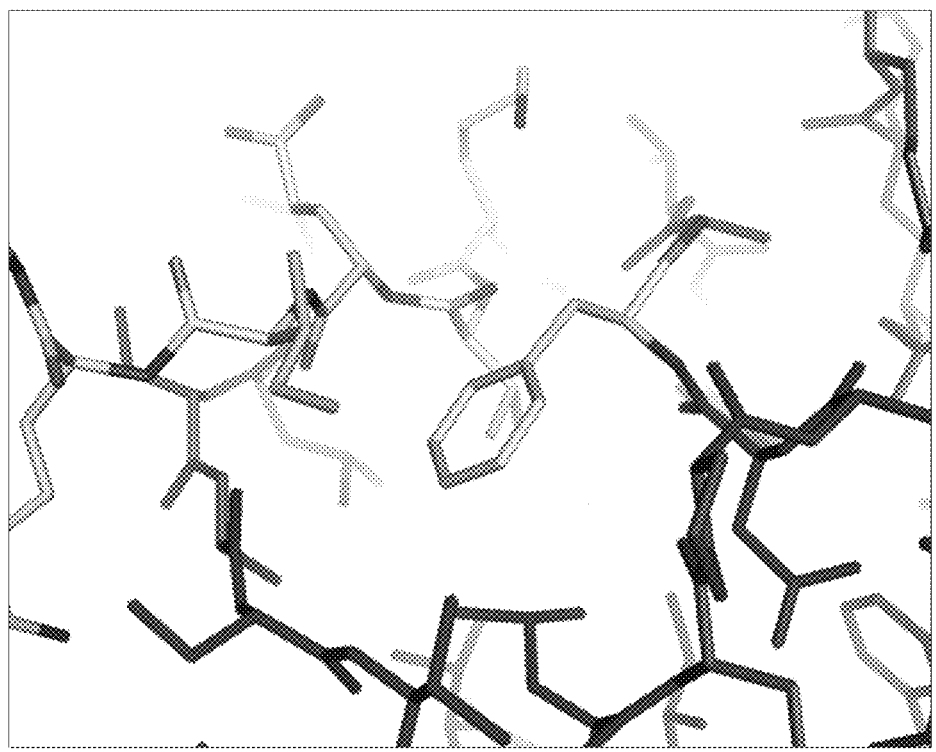
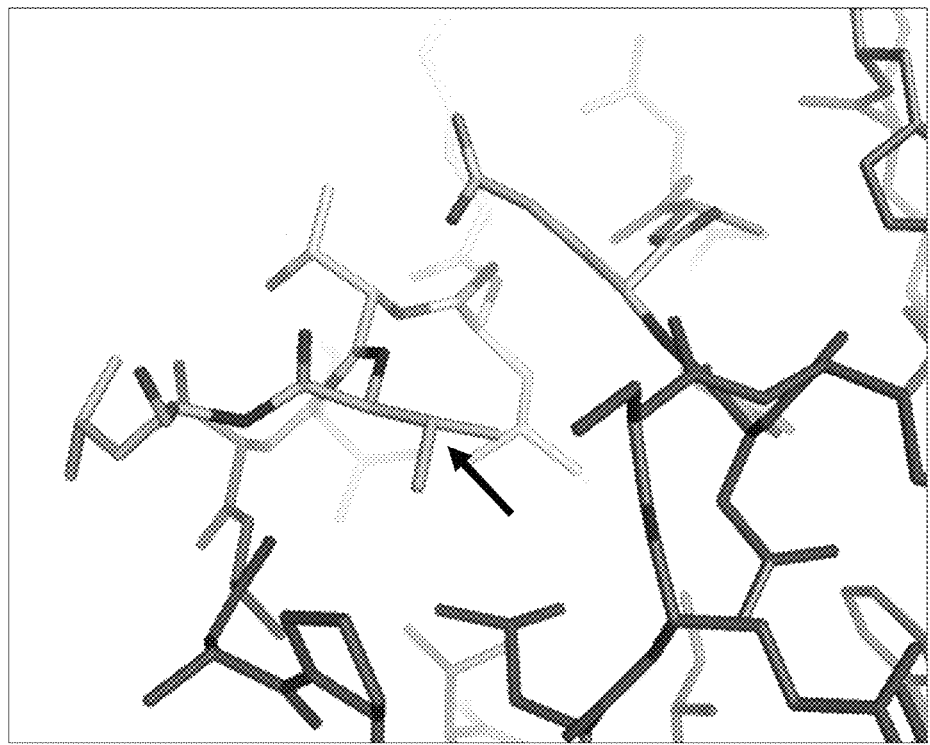

SEQUENCE LISTING

```
<160> NUMBER OF SEQ ID NOS: 42

<210> SEQ ID NO 1
<211> LENGTH: 20
<212> TYPE: PRT
<213> ORGANISM: Artificial Sequence
<220> FEATURE:
<223> OTHER INFORMATION: artificial linker

<400> SEQUENCE: 1

Gly Gly Gly Gly Ser Gly Gly Gly Gly Ser Gly Gly Gly Gly Ser Gly
1               5                   10                  15

Gly Gly Gly Ser
            20

<210> SEQ ID NO 2
<211> LENGTH: 111
<212> TYPE: PRT
<213> ORGANISM: Artificial Sequence
<220> FEATURE:
<223> OTHER INFORMATION: artificial VL sequence

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45
```

Tyr Gly Ala Ser Arg Leu Ala Ser Gly Val Pro Ser Arg Phe Ser Gly
            50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Asp Ser Tyr
                85                  90                  95

Val Asp Asn Leu Phe Gly Gln Gly Thr Lys Val Glu Ile Lys Arg
            100                 105                 110

<210> SEQ ID NO 3
<211> LENGTH: 122
<212> TYPE: PRT
<213> ORGANISM: Artificial Sequence
<220> FEATURE:
<223> OTHER INFORMATION: artificial VH sequence

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Ser Ser Gly
            20                  25                  30

Ala Met Ser Trp Val Arg Gln Ala Pro Gly Lys Gly Leu Glu Trp Ile
        35                  40                  45

Gly Val Ile Ile Ser Ser Gly Ala Thr Tyr Tyr Ala Ser Trp Ala Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Leu Val Thr Val Ser Ser
            115                 120

<210> SEQ ID NO 4
<211> LENGTH: 111
<212> TYPE: PRT
<213> ORGANISM: Artificial Sequence
<220> FEATURE:
<223> OTHER INFORMATION: artificial VL sequence

<400> SEQUENCE: 4

Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
            100                 105                 110

<210> SEQ ID NO 5
<211> LENGTH: 122
<212> TYPE: PRT
<213> ORGANISM: Artificial Sequence
<220> FEATURE:
<223> OTHER INFORMATION: artificial VH sequence

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Ser Ser Gly
            20                  25                  30

Ala Met Ser Trp Val Arg Gln Ala Pro Gly Lys Gly Leu Glu Trp Val
        35                  40                  45

Gly Val Ile Ile Ser Ser Gly Ala Thr Tyr Tyr Ala Ser Trp Ala Lys
    50                  55                  60

Gly Arg Phe Thr Ile Ser Lys Asp Thr Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Gly Gly Pro Asp Asp Ser Asn Ser Met Gly Thr Phe Asp Pro Trp
            100                 105                 110

Gly Gln Gly Thr Leu Val Thr Val Ser Ser
        115                 120
```

<210> SEQ ID NO 6
<211> LENGTH: 111
<212> TYPE: PRT
<213> ORGANISM: Artificial Sequence
<220> FEATURE:
<223> OTHER INFORMATION: artificial VL sequence

<400> SEQUENCE: 6

```
Glu Ile Val Met Thr Gln Ser Pro Ser Thr Leu Ser Ala Ser Val Gly
1               5                   10                  15

Asp Arg Val Ile Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
    50                  55                  60

Ser Gly Ser Gly Ala Glu Phe Thr Leu Thr Ile Ser Ser Leu Gln Pro
65                  70                  75                  80

Asp Asp Phe Ala Thr Tyr Tyr Cys Gln Gln Gly Trp Ser Asp Ser Tyr
                85                  90                  95

Val Asp Asn Leu Phe Gly Gln Gly Thr Lys Val Glu Ile Lys Arg
            100                 105                 110
```

<210> SEQ ID NO 7
<211> LENGTH: 111
<212> TYPE: PRT
<213> ORGANISM: Artificial Sequence
<220> FEATURE:
<223> OTHER INFORMATION: artificial VL sequence

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asp Trp
            20                  25                  30
```

Leu Ala Trp Tyr Gln Gln Lys Pro Gly Lys Ala Pro Lys Leu Leu Ile
            35                  40                  45

Tyr Gly Ala Ser Arg Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: artificial VL sequence

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
            35                  40                  45

Tyr Gly Ala Ser Arg Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Glu Ala Thr Tyr Tyr Cys Gln Gln Gly Trp Ser Asp Ser Tyr
                85                  90                  95

Val Asp Asn Leu Phe Gly Gln Gly Thr Lys Leu Thr Val Leu Gly
            100                 105                 110

<210> SEQ ID NO 9
<211> LENGTH: 111
<212> TYPE: PRT
<213> ORGANISM: Artificial Sequence
<220> FEATURE:
<223> OTHER INFORMATION: artificial VL sequence

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
            35                  40                  45

Tyr Gly Ala Ser Arg Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Asp Ser Tyr
                85                  90                  95

Val Asp Asn Leu Phe Gly Gly Gly Thr Lys Leu Thr Val Leu Gly
            100                 105                 110

```
<210> SEQ ID NO 10
<211> LENGTH: 111
<212> TYPE: PRT
<213> ORGANISM: Artificial Sequence
<220> FEATURE:
<223> OTHER INFORMATION: artificial VL sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Trp Ser Asp Ser Tyr
                85                  90                  95

Val Asp Asn Leu Phe Gly Gln Gly Thr Lys Val Thr Val Leu Gly
            100                 105                 110

<210> SEQ ID NO 11
<211> LENGTH: 111
<212> TYPE: PRT
<213> ORGANISM: Artificial Sequence
<220> FEATURE:
<223> OTHER INFORMATION: artificial VL sequence

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45

Tyr Gly Ala Ser Arg Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Glu Ala Thr Tyr Tyr Cys Gln Gln Gly Trp Ser Asp Ser Tyr
                85                  90                  95

Val Asp Asn Leu Phe Gly Gly Gly Thr Lys Leu Thr Val Leu Gly
            100                 105                 110

<210> SEQ ID NO 12
<211> LENGTH: 111
<212> TYPE: PRT
<213> ORGANISM: Artificial Sequence
<220> FEATURE:
<223> OTHER INFORMATION: artificial VL sequence

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asp Trp
            20                  25                  30

Leu Ala Trp Tyr Gln Gln Lys Pro Gly Lys Ala Pro Lys Leu Leu Ile
        35                  40                  45
```

```
Tyr Gly Ala Ser Arg Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Trp Ser Asp Ser Tyr
                    85                  90                  95

Val Asp Asn Leu Phe Gly Thr Gly Thr Lys Val Thr Val Leu Gly
                100                 105                 110
```

<210> SEQ ID NO 13
<211> LENGTH: 111
<212> TYPE: PRT
<213> ORGANISM: Artificial Sequence
<220> FEATURE:
<223> OTHER INFORMATION: artificial VL sequence

<400> SEQUENCE: 13

```
Asp Ile Gln Met Thr Gln Ser Pro Ser Ser Leu Ser Ala Ser Val Gly
 1               5                  10                  15

Asp Arg Val Thr Ile Thr Cys Gln Ala Ser Gln Ser Ile Ser Asp Trp
                20                  25                  30

Leu Ala Trp Tyr Gln Gln Lys Pro Gly Lys Ala Pro Lys Leu Leu Ile
            35                  40                  45

Tyr Gly Ala Ser Arg Leu Ala Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Glu Ala Thr Tyr Tyr Cys Gln Gln Gly Trp Ser Asp Ser Tyr
                    85                  90                  95

Val Asp Asn Leu Phe Gly Thr Gly Thr Lys Val Thr Val Leu Gly
                100                 105                 110
```

<210> SEQ ID NO 14
<211> LENGTH: 122
<212> TYPE: PRT
<213> ORGANISM: Artificial Sequence
<220> FEATURE:
<223> OTHER INFORMATION: artificial VH sequence

<400> SEQUENCE: 14

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Ser Ser Gly
                20                  25                  30

Ala Met Ser Trp Val Arg Gln Ala Pro Gly Lys Gly Leu Glu Trp Ile
            35                  40                  45

Gly Val Ile Ile Ser Ser Gly Ala Thr Tyr Tyr Ala Ser Trp Ala Lys
        50                  55                  60

Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                    85                  90                  95

Arg Gly Gly Pro Asp Asp Ser Asn Ser Met Gly Thr Phe Asp Pro Trp
                100                 105                 110

Gly Gln Gly Thr Leu Val Thr Val Ser Ser
            115                 120
```

```
<210> SEQ ID NO 15
<211> LENGTH: 11
<212> TYPE: PRT
<213> ORGANISM: Artificial Sequence
<220> FEATURE:
<223> OTHER INFORMATION: artificial VL framewort sequence

<400> SEQUENCE: 15

Phe Gly Gln Gly Thr Lys Leu Thr Val Leu Gly
1               5                   10

<210> SEQ ID NO 16
<211> LENGTH: 11
<212> TYPE: PRT
<213> ORGANISM: Homo sapiens

<400> SEQUENCE: 16

Phe Gly Thr Gly Thr Lys Val Thr Val Leu Gly
1               5                   10

<210> SEQ ID NO 17
<211> LENGTH: 11
<212> TYPE: PRT
<213> ORGANISM: Homo sapiens

<400> SEQUENCE: 17

Phe Gly Gly Gly Thr Lys Leu Thr Val Leu Gly
1               5                   10

<210> SEQ ID NO 18
<211> LENGTH: 11
<212> TYPE: PRT
<213> ORGANISM: Homo sapiens

<400> SEQUENCE: 18

Phe Gly Gly Gly Thr Gln Leu Ile Ile Leu Gly
1               5                   10

<210> SEQ ID NO 19
<211> LENGTH: 11
<212> TYPE: PRT
<213> ORGANISM: Homo sapiens

<400> SEQUENCE: 19

Phe Gly Glu Gly Thr Glu Leu Thr Val Leu Gly
1               5                   10

<210> SEQ ID NO 20
<211> LENGTH: 11
<212> TYPE: PRT
<213> ORGANISM: Homo sapiens

<400> SEQUENCE: 20

Phe Gly Ser Gly Thr Lys Val Thr Val Leu Gly
1               5                   10

<210> SEQ ID NO 21
<211> LENGTH: 11
<212> TYPE: PRT
<213> ORGANISM: Homo sapiens

<400> SEQUENCE: 21

Phe Gly Gly Gly Thr Gln Leu Thr Val Leu Gly
1               5                   10
```

```
<210> SEQ ID NO 22
<211> LENGTH: 11
<212> TYPE: PRT
<213> ORGANISM: Homo sapiens

<400> SEQUENCE: 22

Phe Gly Gly Gly Thr Gln Leu Thr Ala Leu Gly
1               5                   10

<210> SEQ ID NO 23
<211> LENGTH: 108
<212> TYPE: PRT
<213> ORGANISM: Artificial Sequence
<220> FEATURE:
<223> OTHER INFORMATION: artificial VL sequence

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Leu
                85                  90                  95

Thr Phe Gly Gln Gly Thr Lys Val Glu Ile Lys Arg
            100                 105

<210> SEQ ID NO 24
<211> LENGTH: 113
<212> TYPE: PRT
<213> ORGANISM: Artificial Sequence
<220> FEATURE:
<223> OTHER INFORMATION: artificial VL sequence

<400> SEQUENCE: 24

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110

Arg

<210> SEQ ID NO 25
<211> LENGTH: 109
<212> TYPE: PRT
<213> ORGANISM: Artificial Sequence
```

```
<220> FEATURE:
<223> OTHER INFORMATION: artificial VL sequence

<400> SEQUENCE: 25

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Asn Ser Pro
                85                  90                  95

Tyr Thr Phe Gly Gln Gly Thr Lys Val Glu Ile Lys Arg
            100                 105

<210> SEQ ID NO 26
<211> LENGTH: 114
<212> TYPE: PRT
<213> ORGANISM: Artificial Sequence
<220> FEATURE:
<223> OTHER INFORMATION: artificial VL sequence

<400> SEQUENCE: 26

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Pro Thr Phe Gly Gln Gly Thr Lys Val Glu Ile
            100                 105                 110

Lys Arg

<210> SEQ ID NO 27
<211> LENGTH: 119
<212> TYPE: PRT
<213> ORGANISM: Artificial Sequence
<220> FEATURE:
<223> OTHER INFORMATION: artificial VH sequence

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Gly Tyr Cys Ser Gly Phe Asp Tyr Trp Gly Gln Gly
                100                 105                 110

Thr Leu Val Thr Val Ser Ser
        115

<210> SEQ ID NO 28
<211> LENGTH: 117
<212> TYPE: PRT
<213> ORGANISM: Artificial Sequence
<220> FEATURE:
<223> OTHER INFORMATION: artificial VH sequence

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Asn Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Asp Gly Asp Gly Gly Phe Asp Tyr Trp Gly Gln Gly Thr Leu
                100                 105                 110

Val Thr Val Ser Ser
        115

<210> SEQ ID NO 29
<211> LENGTH: 120
<212> TYPE: PRT
<213> ORGANISM: Artificial Sequence
<220> FEATURE:
<223> OTHER INFORMATION: artificial VH sequence

<400> SEQUENCE: 29

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Ala Leu Glu
            35                  40                  45

Trp Leu Ala His Ile Asp Trp Asp Asp Lys Tyr Tyr Ser Thr Ser
        50                  55                  60

Leu Lys Ser Arg Leu Thr Ile Ser Lys Asp Ser Lys Asn Gln Val
65                  70                  75                  80

Val Leu Thr Met Thr Asn Met Asp Pro Val Asp Thr Ala Thr Tyr Tyr
                85                  90                  95
```

```
Cys Ala Arg Ile His Asn Ile Gly Glu Ala Phe Asp Val Trp Gly Gln
            100                 105                 110

Gly Thr Leu Val Thr Val Ser Ser
        115                 120

<210> SEQ ID NO 30
<211> LENGTH: 117
<212> TYPE: PRT
<213> ORGANISM: Artificial Sequence
<220> FEATURE:
<223> OTHER INFORMATION: artificial VH sequence

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Val Ile Ser Tyr Asp Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ser Gly Asp Tyr Trp Gly Gln Gly Thr Leu
            100                 105                 110

Val Thr Val Ser Ser
        115

<210> SEQ ID NO 31
<211> LENGTH: 118
<212> TYPE: PRT
<213> ORGANISM: Artificial Sequence
<220> FEATURE:
<223> OTHER INFORMATION: artificial VH sequence

<400> SEQUENCE: 31

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Glu Ile Tyr His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Gly Gly Gly Val Phe Asp Tyr Trp Gly Gln Gly Thr
            100                 105                 110

Leu Val Thr Val Ser Ser
        115

<210> SEQ ID NO 32
<211> LENGTH: 119
<212> TYPE: PRT
<213> ORGANISM: Artificial Sequence
```

```
<220> FEATURE:
<223> OTHER INFORMATION: artificial VH sequence

<400> SEQUENCE: 32

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Leu Gly Gly Gly Gly Tyr Tyr Phe Asp Tyr Trp Gly Gln Gly
            100                 105                 110

Thr Leu Val Thr Val Ser Ser
        115

<210> SEQ ID NO 33
<211> LENGTH: 119
<212> TYPE: PRT
<213> ORGANISM: Artificial Sequence
<220> FEATURE:
<223> OTHER INFORMATION: artificial VH sequence

<400> SEQUENCE: 33

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Gly Phe Asp Val Trp Gly Gln Gly
            100                 105                 110

Thr Leu Val Thr Val Ser Ser
        115

<210> SEQ ID NO 34
<211> LENGTH: 23
<212> TYPE: PRT
<213> ORGANISM: Artificial Sequence
<220> FEATURE:
<223> OTHER INFORMATION: artificial VL sequence

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys
            20
```

-continued

```
<210> SEQ ID NO 35
<211> LENGTH: 15
<212> TYPE: PRT
<213> ORGANISM: Artificial Sequence
<220> FEATURE:
<223> OTHER INFORMATION: artificial VL sequence

<400> SEQUENCE: 35

Trp Tyr Gln Gln Lys Pro Gly Lys Ala Pro Lys Leu Leu Ile Tyr
1               5                   10                  15

<210> SEQ ID NO 36
<211> LENGTH: 32
<212> TYPE: PRT
<213> ORGANISM: Artificial Sequence
<220> FEATURE:
<223> OTHER INFORMATION: artificial VL sequence

<400> SEQUENCE: 36

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 37
<211> LENGTH: 11
<212> TYPE: PRT
<213> ORGANISM: Artificial Sequence
<220> FEATURE:
<223> OTHER INFORMATION: artificial VL sequence

<400> SEQUENCE: 37

Phe Gly Gln Gly Thr Lys Val Glu Ile Lys Arg
1               5                   10

<210> SEQ ID NO 38
<211> LENGTH: 25
<212> TYPE: PRT
<213> ORGANISM: Artificial Sequence
<220> FEATURE:
<223> OTHER INFORMATION: artificial VH sequence

<400> SEQUENCE: 38

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 39
<211> LENGTH: 14
<212> TYPE: PRT
<213> ORGANISM: Artificial Sequence
<220> FEATURE:
<223> OTHER INFORMATION: artificial VH sequence

<400> SEQUENCE: 39

Trp Val Arg Gln Ala Pro Gly Lys Gly Leu Glu Trp Val Ser
1               5                   10

<210> SEQ ID NO 40
<211> LENGTH: 31
<212> TYPE: PRT
<213> ORGANISM: Artificial Sequence
<220> FEATURE:
<223> OTHER INFORMATION: artificial VH sequence
```

```
<400> SEQUENCE: 40

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala
                20                  25                  30

<210> SEQ ID NO 41
<211> LENGTH: 11
<212> TYPE: PRT
<213> ORGANISM: Artificial Sequence
<220> FEATURE:
<223> OTHER INFORMATION: artificial VH sequence

<400> SEQUENCE: 41

Trp Gly Gln Gly Thr Leu Val Thr Val Ser Ser
1               5                   10

<210> SEQ ID NO 42
<211> LENGTH: 15
<212> TYPE: PRT
<213> ORGANISM: Artificial Sequence
<220> FEATURE:
<223> OTHER INFORMATION: artifcial linker

<400> SEQUENCE: 42

Gly Gly Gly Gly Ser Gly Gly Gly Gly Ser Gly Gly Gly Gly Ser
1               5                   10                  15
```

ANTIBODY FRAMEWORKS

CROSS-REFERENCE TO RELATED APPLICATIONS

This application is a division of U.S. patent application Ser. No. 14/900,550 filed Dec. 21, 2015, which is a 371 national phase of International Patent Application No. PCT/EP2014/001730 filed Jun. 26, 2014, which claims priority to European Patent Application No. 13003264.2 filed Jun. 26, 2013, the content of each of which applications is incorporated herein by reference.

SEQUENCE LISTING

This application contains a sequence listing submitted electronically via EFS-web, which serves as both the paper copy and the computer readable form (CRF) and consists of a file entitled "WR-PAT-N4DIV1_seqlist.txt", which was created on Oct. 7, 2018, which is 30,801 bytes in size, and which is herein incorporated by reference in its entirety.

FIELD OF THE INVENTION

The present invention relates to novel antibody frameworks with advantageous properties.

BACKGROUND OF THE INVENTION

This invention relates to novel chimeric human antibody light chain frameworks, comprising framework regions I to III from Vκ and framework region IV from Vλ, with advantageous properties, such as high stability and reduced aggregation propensity.

In the past forty years since the development of the first monoclonal antibodies ("mAbs"; Köhler & Milstein, Nature. 256 (1975) 495-7), antibodies have become an increasingly important class of biomolecules for research, diagnostic and therapeutic purposes. Initially, antibodies were exclusively obtained by immunizing animals with the corresponding antigen of interest. While antibodies of non-human origin can be used in research and diagnostics, in therapeutic approaches the human body may recognize non-human antibodies as foreign and raise an immune response against the non-human antibody drug substance, rendering it less or not effective. Thus, recombinant methods have been set up to render non-human antibodies less immunogenic.

Initial efforts to convert non-human mAbs into less immunogenic therapeutics entailed the engineering of chimeric antibodies consisting of animal (for example rodent) variable domains and human constant regions (Boulianne et al., Nature 312, (1984) 643-646). Further approaches aimed at the humanization of the rodent mAbs by introducing the CDRs in human variable domain scaffolds (Jones et al. Nature 321 (1986) 522-525; Riechmann et al., Nature 332 (1988) 323-7) or by resurfacing the variable domains (Roguska et al., Proc. Natl. Acad. Sci. USA 91 (1994) 969-973).

For the humanization by CDR loop grafting a human acceptor framework is either chosen based on homology to the donor framework (e.g. Roguska et al., Protein Engineering 9 (1996) 895-904; WO/2008/144757 (for rabbits)) or based on a preferred stability profile (Ewert et al., Methods 34 (2004) 184-199). The latter concept has been utilized for the humanization of rabbit antibodies onto a universal variable domain framework (U.S. Pat. No. 8,193,235).

With any chosen approach the resulting mAb or functional fragment ideally retains the desired pharmacodynamic properties of the donor mAb, while displaying drug-like biophysical properties and minimal immunogenicity. With respect to the biophysical properties of mAbs or functional fragments thereof, the propensity for aggregation has been a major concern for the developability of therapeutic molecules, mainly for the following three reasons:

First, protein aggregates generally show a higher potential to elicit an immune reaction in the host leading to the formation of anti-drug antibodies and eventually to drug neutralizing antibodies (Joubert et al., J. Biol. Chem. 287 (2012) 25266-25279).

Second, aggregates affect the manufacturing yield due to the increased effort for their removal (Cromwell et al., AAPS Journal 8 (2006), Article 66).

Third, off-target effects may be observed. The concern about oligomer formation is even more pronounced for applications where monovalent binding is preferred, including bispecific (or multi-specific) antibody formats with only one valency per target and construct, because oligomer formation in these cases results in protein conglomerates with multivalent binding properties potentially leading to off-target effects. An example for such unspecific activities is the use of a construct with a single CD3ε-binding domain in a bispecific antibody format. Such a format may for example bind with one of its two binding domains to a cancer antigen and with its second, CD3ε-binding domain recruiting cytotoxic T cells. Because cross-linking of the monovalent CD3ε-binding moiety is required to induce signaling through CD3ε, T cells will only be stimulated when engaged by multiple bispecific constructs bound to the surface of the target cell—and therefore adopting the properties of a cross-linked molecule—resulting in a specific T cell response that is exclusively directed towards the cancer cell. On the contrary, oligomers of such a construct would exhibit the properties of a cross-linked bispecific antibody and therefore activate cytotoxic T cells, even when not bound to cancer cells, thereby leading to systemic activation of T cells. Such unspecific and systemic activation of T cells could result is elevated cytokine levels leading to adverse effects.

Furthermore, a reliable and universally applicable acceptor framework is beneficial to enable a robust method of humanizing non-human antibodies, since cloning, expression and purification methods may be standardized.

To meet the above mentioned criteria for the humanization of non-human mAbs the published methodology proposes the use of human consensus variable domain framework sequences as acceptor scaffold for the engraftment of non-human complementarity determining regions. Based on the assumption that for each amino acid position in a protein, residues that contribute to protein stability have been enriched in the pool of germ line sequences during evolution, it is the common understanding that the closer the resulting humanized variable domains are to the human germ line consensus sequence of the respective variable domain family, the higher is the expected stability. This concept as described by Steipe (Steipe et al., J. Mol. Biol. 1994 240 (1994) 188-92) and reviewed by Worn (Worn et al., J. Mol. Biol. 305 (2001) 989-1010) is widely accepted and finds wide-ranging application. Non-limiting examples are (a) the use of consensus sequence variable domains for the humanization of non-human antibodies (Carter et al., Proc. Natl. Acad. Sci. USA 89 (1992) 4285-4289); (b) the use of consensus sequence variable domains to construct CDR libraries for in vitro screening of stable target-binding antibodies (Knappik et al., J. Mol. Biol. 296 (2000) 57-86); and (c) knowledge-based approaches to improve stability of antibody variable domains by exchanging non-consensus residues into consensus residues (Steipe, loc. cit.).

In addition, stabilities of the different variable domain families are described with VH3 being the most stable variable heavy domain. Importantly, in case of the variable light chain domains the Vκ family rather than the Vλ family is preferred (Ewert, loc. cit.). In particular, the human consensus sequences of VH3 and Vκ1 have been described as having favorable biophysical properties (Ewert, loc. cit.) and as being particularly suitable for the humanization of antibodies from non-human sources (use in Carter, loc. cit.).

In line with this there are several publications, in which the human Vκ1-VH3 consensus framework hu-4D5 has been used for the humanization of rodent and rabbit antibodies (Rader, J. Biol. Chem. 275 (2000) 13668-13676; WO/2005/016950; WO 2008/004834). Alternatively, a naturally occurring sequence belonging to the same families as hu-4D5 has been used to generate stable humanized single-chain (scFv) fragments from rabbit origin (U.S. Pat. No. 8,293,235; Borras et al., J. Biol. Chem. 285 (2010) 9054-9066).

Importantly it has to be noted that natural selection evolved stable variable domains always in the context of full-length antibodies, in which the variable domain is adjacent to and in contact with the constant domain 1. Therefore, it may well be that certain non-consensus residues provide better stability to the isolated variable domains, for example in the context of the single-chain Fv (scFv) fragment. In support with this hypothesis, non-consensus mutations contributing to stability have been described in US patent application US 2009/0074780.

Additionally, antibody stability is of crucial importance for production, purification, shelf-life and, as a consequence, the cost of goods for antibody therapeutics. Even minor improvements in one or more of these parameters may be highly relevant for the question of whether research and development of an antibody drug are going to be commercially viable.

Thus, despite that fact that many attempts have already been made to address the issue of obtaining humanized antibody drug substances from non-human antibodies, there still remains a large unmet need to develop novel human antibody frameworks with advantageous properties, such as high stability and reduced aggregation propensity, wherein the human antibody frameworks contain as few mutations as possible, ideally none, when compared to naturally occurring sequences, in order to reduce the risk of creating immunogenic sequences as far as possible. Such stable human frameworks could also be used to stabilize fully human antibodies or fragments thereof for example by loop grafting or simply by exchanging the stability-contributing component between the parent antibody and the stable framework.

The solution for this problem that has been provided by the present invention, i.e. novel chimeric human antibody light chain frameworks, comprising framework regions I to III from Vκ and framework region IV from Vλ, with advantageous properties, such as high stability and reduced aggregation propensity, has so far not been achieved or suggested by the prior art.

SUMMARY OF THE INVENTION

The present invention relates to novel chimeric human antibody light chain frameworks, comprising framework regions I to III from Vκ and framework region IV from Vλ, with advantageous properties, such as high stability, reduced aggregation propensity and minimal immunogenic potential.

Thus, in a first aspect, the present invention relates to an antibody VL domain comprising (i) human Vκ framework regions I to III; (ii) CDR domains CDR1, CDR2 and CDR3; and (iii) a framework region IV, which is selected from a. a human Vλ germ line sequence for framework region IV, particularly a Vλ germ line sequence selected from the list of: SEQ ID NO. 16 to 22;

b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and c. a Vλ-based sequence, which has one or two mutations, particularly one mutation, compared to the closest human Vλ germ line sequence for framework region IV;

provided that if, in case of b. or c, framework region IV has the sequence FGQGTKLTVLG (SEQ ID No. 15)

(w) said human Vκ framework regions I to III are different from the framework regions as found in the list of clones: FW1.4gen (SEQ ID NO: 4), 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, and 43-FW1.4opt;

(x) said human Vκ framework regions I to III are different from a sequence obtainable by permutation from the sequences of the framework regions as found in the list of clones: FW1.4gen (SEQ ID NO: 4), 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, and 43-FW1.4opt;

(y) said human Vκ framework regions I to III are different from a sequence obtainable by mutation of the sequence FW1.4gen (SEQ ID NO: 4) at one or more of positions 15, 22, 48, 57, 74, 87, 88, 90, 92, 95, 97 and 99 (AHo numbering); or (z) said human Vκ framework regions I to III comprise not more than five mutations compared to the respective regions in the human Vκ sequence with SEQ ID No: 8, particularly less than five, less than four, less than three, particularly only one or no mutation compared to the human Vκ sequence with SEQ ID No: 8.

In a second aspect, the present invention relates to an isolated antibody or functional fragment thereof comprising an antibody VL domain according to the present invention.

In a third aspect, the present invention relates to a pharmaceutical composition comprising the isolated antibody or functional fragment thereof of the present invention, and optionally a pharmaceutically acceptable carrier and/or excipient.

In a fourth aspect, the present invention relates to a nucleic acid sequence or a collection of nucleic acid sequences encoding the antibody VL domain of any one of the present invention, or the isolated antibody or functional fragment thereof of the present invention, and/or to a nucleic acid sequence or nucleic acid sequences obtainable by the method according to the ninth aspect of the present invention.

In a fifth aspect, the present invention relates to a vector or a collection of vectors comprising the nucleic acid sequence or a collection of nucleic acid sequences of the present invention.

In a sixth aspect, the present invention relates to a host cell, particularly an expression host cell, comprising the nucleic acid sequence or the collection of nucleic acid sequences of the present invention, or the vector or collection of vectors of the present invention.

In a seventh aspect, the present invention relates to a method for producing the antibody VL domain of any one of the present invention, or the isolated antibody or functional fragment thereof of the present invention, comprising the step of expressing the nucleic acid sequence or the collection of nucleic acid sequences of the present invention, or the vector or collection of vectors of the present invention, or the host cell, particularly an expression host cell, of the present invention.

In an eighth aspect, the present invention relates to a method for generating a humanized rabbit antibody comprising the steps of:
a) immunization of rabbits with an antigen of interest;
b) isolating at least one antibody of interest; and
c) cloning of the VL CDR regions of said at least one antibody of interest into a nucleic acid sequence encoding an antibody VL domain according to the present invention.

In a ninth aspect, the present invention relates to a method for generating a nucleic acid sequence encoding an antibody VL domain according to the present invention, or one or more nucleic acid sequences encoding an isolated antibody or functional fragment thereof according to the present invention, comprising combining in one or more steps nucleic acid sequences encoding (i) human Vκ framework regions I to III; (ii) CDR domains CDR1, CDR2 and CDR3, and (iii) a framework region IV, which is selected from
  a. a human Vλ germ line sequence for framework region IV, particularly a Vλ germ line sequence selected from the list of: SEQ ID NO. 16 to 22;
  b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and
  c. a Vλ-based sequence, which has one or two mutations, particularly one mutation, compared to the closest human Vλ germ line sequence for framework region IV;
particularly using one of the following methods:
  i. replacing in a nucleic acid construct, particularly in a recombinant vector, comprising a nucleic acid sequence encoding a human or humanized Vκ domain the Vκ framework region IV by a framework region IV, which is selected from
    a. a human Vλ germ line sequence for framework region IV, particularly a Vλ germ line sequence selected from the list of: SEQ ID NO. 16 to 22;
    b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and
    c. a Vλ-based sequence, which has one or two mutations, particularly one mutation, compared to the closest human Vλ germ line sequence for framework region IV;
  ii. inserting in one or more steps into a nucleic acid construct, particularly into a recombinant vector, comprising a nucleic acid sequence encoding a framework region IV one or more nucleic acid sequences encoding (i) human Vκ framework regions I to III; and (ii) CDR domains CDR1, CDR2 and CDR3, wherein said framework region IV is selected from
    a. a human Vλ germ line sequence for framework region IV, particularly a Vλ germ line sequence selected from the list of: SEQ ID NO. 16 to 22;
    b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and
    c. a Vλ-based sequence, which has one or two mutations, particularly one mutation, compared to the closest human Vλ germ line sequence for framework region IV;
  iii. mutating in a nucleic acid sequence encoding a human or humanized Vκ domain the nucleic acid sequence encoding framework region IV to generate a framework region IV, which is selected from
    a. a human Vλ germ line sequence for framework region IV, particularly a Vλ germ line sequence selected from the list of: SEQ ID NO. 16 to 22;
    b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and
    c. a Vλ-based sequence, which has one or two mutations, particularly one mutation, compared to the closest human Vλ germ line sequence for framework region IV; or
  iv. replacing in one or more steps in a nucleic acid construct, particularly in a recombinant vector, comprising a nucleic acid sequence encoding a light chain domain comprising human Vκ framework regions I to III, CDR domains CDR1, CDR2 and CDR3, and a framework region IV, one or more of the nucleic acid sequences encoding said CDR domains by nucleic acid sequence(s) encoding the corresponding CDR domain(s) from an antibody of interest, wherein said framework region IV is selected from
    a. a human Vλ germ line sequence for framework region IV, particularly a Vλ germ line sequence selected from the list of: SEQ ID NO. 16 to 22;
    b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and c. a Vλ-based sequence, which has one or two mutations, particularly one mutation, compared to the closest human Vλ germ line sequence for framework region IV.

BRIEF DESCRIPTION OF THE DRAWINGS

FIG. 2 shows a sequence alignment of the variable domain sequences of hu-4D5 and of the tested alternative frameworks. Differences to hu-4D5 are indicated in black. For hu-4D5, only the framework regions Vκ frameworks I to IV (SEQ ID NOs: 34 to 37) and VH frameworks I to IV (SEQ ID NOs: 38 to 41) are shown.

FIG. 4 shows a model of the interaction between framework III residue AHo101 and the lambda joining region (framework IV); VL Kappa (top; PDB ID:1 FVC) and VL Lambda (bottom; PDB ID 2A9M).

DETAILED DESCRIPTION OF THE INVENTION

Figure 1:
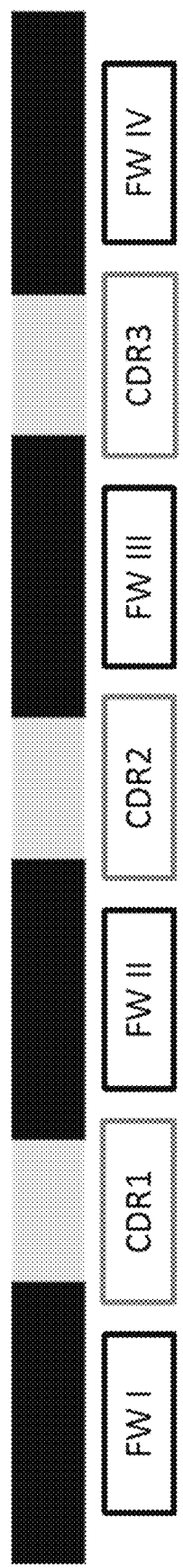
FIG. 1 shows the variable domain topology outlining the framework and CDR regions.

The peculiarity of this invention compared to former approaches for creating human frameworks for the humanization/stabilization of non-human antibodies or the stabilization of human antibodies is the fact that the present inventions relates to the replacement of a κ joining segment in a κ variable light domain by a λ joining segment (framework region IV) resulting in a κ–λ chimeric variable light domain with improved protein stability and reduced aggregation propensity. It further relates to the mutation of the κ consensus residue at position AHo101 (framework region III) and replacement by a λ consensus residue to support packing of the λ joining segment in a κ–λ chimeric variable light domain to further improve protein stability and to further reduce aggregation propensity.

Thus, in a first aspect, the present invention relates to an antibody VL domain comprising (i) human Vκ framework regions I to III; (ii) CDR domains CDR1, CDR2 and CDR3; and (iii) a framework region IV, which is selected from a. a human Vλ germ line sequence for framework region IV, particularly a Vλ germ line sequence selected from the list of: SEQ ID NO. 16 to 22;

b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and c. a Vλ-based sequence, which has one or two mutations, particularly one mutation, compared to the closest human Vλ germ line sequence for framework region IV;

provided that if, in case of b. or c, framework region IV has the sequence FGQGTKLTVLG (SEQ ID No. 15)

(w) said human Vκ framework regions I to III are different from the framework regions as found in the list of clones: FW1.4gen (SEQ ID NO: 4), 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, and 43-FW1.4opt;

(x) said human Vκ framework regions I to III are different from a sequence obtainable by permutation from the sequences of the framework regions as found in the list of clones: FW1.4gen (SEQ ID NO: 4), 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, and 43-FW1.4opt;

(y) said human Vκ framework regions I to III are different from a sequence obtainable by mutation of the sequence FW1.4gen (SEQ ID NO: 4) at one or more of positions 15, 22, 48, 57, 74, 87, 88, 90, 92, 95, 97 and 99 (AHo numbering); or (z) said human Vκ framework regions I to III comprise not more than five mutations compared to the respective regions in the human Vκ sequence with SEQ ID No: 8, particularly less than five, less than four, less than three, particularly only one or no mutation compared to the human Vκ sequence with SEQ ID No: 8.

In the context of the present invention, the clones 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, and 43-FW1.4opt refer to the clones listed in Borras et al. (loc. cit.). These clones are variants of the VL domain FW1.4gen (SEQ ID NO: 4), which differ in certain positions in the VL framework regions from those of FW1.4gen (SEQ ID NO: 4) as shown in Table 5.

In a particular embodiment, said framework region IV is not FGQGTKLTVLG (SEQ ID No. 15).

In the context of the present invention, the term "antibody" is used as a synonym for "immunoglobulin" (Ig), which is defined as a protein belonging to the class IgG, IgM, IgB, IgA, or IgD (or any subclass thereof), and includes all conventionally known antibodies and functional fragments thereof. A "functional fragment" of an antibody/immunoglobulin is defined as a fragment of an antibody/immunoglobulin (e.g., a variable region of an IgG) that retains the antigen-binding region. An "antigen-binding region" of an antibody typically is found in one or more hypervariable region(s) of an antibody, i.e., the CDR-1, -2, and/or -3 regions; however, the variable "framework" regions can also play an important role in antigen binding, such as by providing a scaffold for the CDRs.

In the context of the present invention, the numbering system suggested by Honegger & Plückthun is used (Honegger & Plückthun, J. Mol. Biol. 309 (2001) 657-670), unless specifically mentioned otherwise, Furthermore, the following residues are defined as CDR regions: CDR-L1: L24-L42; CDR-L2: L58-L72; CDR-L3: L107-L138; CDR-H1: H27-H42; CDR-H2: H57-H76; CDR-H3: H109-H138. Preferably, the "antigen-binding region" comprises at least amino acid residues 4 to 149 of the variable light (VL) chain and 5 to 144 of the variable heavy (VH) chain, more preferably amino acid residues 3 to 149 of VL and 4 to 146 of VH, and particularly preferred are the complete VL and VH chains (amino acid positions 1 to 149 of VL and 1 to 149 of VH; numbering according to FIG. 2). The framework and CDR regions are indicated in FIG. 2. A preferred class of immunoglobulins for use in the present invention is IgG. "Functional fragments" of the invention include the domain of a F(ab')$_2$ fragment, a Fab fragment and scFv. The F(ab')2 or Fab may be engineered to minimize or remove the intermolecular disulphide interactions that occur between the CH1 and CL domains. The antibodies or functional fragments thereof of the present invention may be part of bi- or multifunctional constructs, as further described in Sections [0055] to [0058].

In the context of the present invention the terms "Vκ" and "Vλ" refer to families of antibody light chain sequences that are grouped according to sequence identity and homology. Methods for the determination of sequence homologies, for example by using a homology search matrix such as BLOSUM (Henikoff, S. & Henikoff, J. G., Proc. Natl. Acad. Sci. USA 89 (1992) 10915-10919), and methods for the grouping of sequences according to homologies are well known to one of ordinary skill in the art. For both Vκ and Vλ different subfamilies can be identified (see, for example, Knappik, loc. cit., which groups Vκ in Vκ1 to Vκ4 and Vλ in Vλ1 to Vλ3).

In the context of the present invention, the term "a sequence obtainable by permutation from the sequences of the framework regions as found in the list of clones: . . . " refers to sequences that can be created by using (i) either the amino acid residue present at a given position in all sequences comprised in said list (see Borras, loc. cit.) or (ii) for the positions that have been optimized in Borras (Borras, loc. cit.), any one of the amino acid residues present at one of the diversified position in said sequences (positions 15, 22, 40, 49, 58, 69, 70, 72, 74, 77, 79, and 81 in Borras (Borras, loc. cit.); corresponding to AHo positions 15, 22, 48, 57, 74, 87, 88, 90, 92, 95, 97 and 99).

In one embodiment of the present invention, the amino acid residue in position AHo101 (position 101 according to the numbering system of Honegger and Plückthun) in framework region III is an amino acid residue present at that position in a human Vλ consensus sequence, particularly wherein said amino acid residue is different from phenylalanine, more particularly wherein said amino acid residue is glutamic acid.

In one embodiment of the present invention, said Vκ framework regions I to III belong to a Vκ domain subfamily selected from Vκ1, Vκ2, Vκ3, and Vκ4, particularly to the Vκ1 family.

In the context of the present invention, the Vκ domain subfamilies are represented by the consensus sequences shown in SEQ ID NOs: 23 to 26. A given antibody variable light chain domain is regarded as belonging to a Vκ domain subfamily, if it shows the highest degree of sequence homology with said Vκ domain subfamily, when using the methods listed in Section [0039].

In particular embodiments, the Vκ framework regions I to III comprise not more than five mutations compared to (a) the closest human germ line sequence, or (b) one of the consensus sequences with SEQ ID NOs: 23 to 26, particularly SEQ ID NO: 23; particularly less than five, less than four, less than three, particularly only one or no mutation compared to (a) the closest human germ line sequence, or (b) one of the consensus sequences with SEQ ID NOs: 23 to 26, particularly SEQ ID NO: 23.

In one embodiment of the present invention, said Vκ framework regions I to III are the framework regions present in a sequence selected from SEQ ID NO: 2 and SEQ ID NO: 8, particularly SEQ ID NO: 8.

In one embodiment of the present invention, said CDR domains CDR1, CDR2 and CDR3 are independently selected from (i) CDR domains CDR1, CDR2 and CDR3 from a parental non-human antibody with specificity for an antigen of interest, particularly from a parental rabbit antibody or from a parental rodent antibody, particularly a parental mouse or rat antibody; (ii) CDR domains CDR1, CDR2 and CDR3 from a parental human or humanized antibody comprising a Vκ domain, particularly from an antibody approved for therapy or otherwise being commercialized; (iii) CDR domains CDR1, CDR2 and CDR3 derived from the CDR domains according to (i) or (ii), particularly CDR domains obtained by optimizing one or more of the CDR domains according to (i) or (ii); and (iv) a CDR domain to be replaced by one or more CDR domains according to (i), (ii) and/or (iii).

In one embodiment of the present invention, the framework regions I to IV are a combination of framework regions as found in a sequence selected from: SEQ ID NO: 8, SEQ ID NO: 9, SEQ ID NO: 11, SEQ ID NO: 12, and SEQ ID NO: 13.

In a second aspect, the present invention relates to an isolated antibody or functional fragment thereof comprising an antibody VL domain according to the present invention.

In particular embodiments, the antibody VL domain has binding specificity for a target of interest.

As used herein, a binding molecule is "specific to/for", "specifically recognizes", or "specifically binds to" a target, such as for example human CD3, when such binding molecule is able to discriminate between such target biomolecule and one or more reference molecule(s), since binding specificity is not an absolute, but a relative property. In its most general form (and when no defined reference is mentioned), "specific binding" is referring to the ability of the binding molecule to discriminate between the target biomolecule of interest and an unrelated biomolecule, as determined, for example, in accordance with a specificity assay methods known in the art. Such methods comprise, but are not limited to Western blots, ELISA, RIA, ECL, IRMA tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. Typically, determination of binding specificity is performed by using not a single reference biomolecule, but a set of about three to five unrelated biomolecules, such as milk powder, BSA, transferrin or the like.

In the context of the present invention, the term "about" or "approximately" means between 90% and 110% of a given value or range.

However, "specific binding" also may refer to the ability of a binding molecule to discriminate between the target biomolecule and one or more closely related biomolecule(s), which are used as reference points. Additionally, "specific binding" may relate to the ability of a binding molecule to discriminate between different parts of its target antigen, e.g. different domains, regions or epitopes of the target biomolecule, or between one or more key amino acid residues or stretches of amino acid residues of the target biomolecule.

In the context of the present invention, the term "epitope" refers to that part of a given target biomolecule that is required for specific binding between the target biomolecule and a binding molecule. An epitope may be continuous, i.e. formed by adjacent structural elements present in the target biomolecule, or discontinuous, i.e. formed by structural elements that are at different positions in the primary sequence of the target biomolecule, such as in the amino acid sequence of a protein as target, but in close proximity in the three-dimensional structure, which the target biomolecule adopts, such as in the bodily fluid.

In one embodiment of the present invention, the isolated antibody or functional fragment thereof is selected from: an IgG antibody, a Fab and an scFv fragment.

In another particular embodiment of the present invention, the isolated antibody or functional fragment thereof is a bispecific construct which is an antibody format selected from the group consisting of a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tri(a)body, bispecific Fab2, di-miniantibody, tetrabody, scFv-Fc-scFv fusion, di-diabody, DVD-Ig, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), and Knob-into-Holes (KiHs) (bispecific IgGs prepared by the KiH technology) and DuoBodies (bispecific IgGs prepared by the Duobody technology). Particularly suitable for use herein is a single-chain diabody (scDb), in particular a bispecific monomeric scDb.

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VHA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for the second antigen.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. The middle linker L2 particularly is a peptide of 10-40 amino acids, more particularly 15-30 amino acids, and most particularly 20-25 amino acids.

The bispecific constructs of the present invention can be produced using any convenient antibody manufacturing method known in the art (see, e.g., Fischer, N. & Leger, O., Pathobiology 74 (2007) 3-14 with regard to the production of bispecific constructs; Hornig, N. & Farber-Schwarz, A., Methods Mol. Biol. 907 (2012)713-727, and WO 99/57150 with regard to bispecific diabodies and tandem scFvs). Specific examples of suitable methods for the preparation of the bispecific construct of the present invention further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

These methods typically involve the generation of monoclonal antibodies, for example by means of fusing myeloma cells with the spleen cells from a mouse that has been immunized with the desired antigen using the hybridoma technology (see, e.g., Yokoyama et al., Curr. Protoc. Immunol. Chapter 2, Unit 2.5, 2006) or by means of recombinant antibody engineering (repertoire cloning or phage display/yeast display) (see, e.g., Chames & Baty, FEMS Microbiol. Letters 189 (2000) 1-8), and the combination of the antigen-binding domains or fragments or parts thereof of two different monoclonal antibodies to give a bispecific construct using known molecular cloning techniques.

In one embodiment of the present invention, the isolated antibody or functional fragment thereof comprises a VH domain belonging to a VH domain subfamily selected from VH1A, VH1B, VH2, VH3, VH4, VH5, and VH6, particularly to a VH domain subfamily VH3 or VH4, particularly to the VH domain subfamily VH3.

In the context of the present invention, the VH domain subfamilies are represented by the consensus sequences shown in SEQ ID NOs: 27 to 33. A given antibody variable heavy chain domain is regarded as belonging to a VH domain subfamily, if it shows the highest degree of sequence homology with said VH domain subfamily, when using the methods listed in Section [0039].

In particular embodiments, the VH domain comprises not more than five mutations compared to (a) the closest human germ line sequence, or (b) one of the consensus sequences with SEQ ID NOs: 28 to 34, particularly SEQ ID NOs: 30; particularly less than five, less than four, less than three, particularly only one or no mutation compared to (a) the closest human germ line sequence, or (b) one of the consensus sequences with SEQ ID NOs: 27 to 33, particularly SEQ ID NOs: 30.

In a third aspect, the present invention relates to a pharmaceutical composition comprising the isolated antibody or functional fragment thereof of the present invention, and optionally a pharmaceutically acceptable carrier and/or excipient.

In a fourth aspect, the present invention relates to a nucleic acid sequence or a collection of nucleic acid sequences encoding the antibody VL domain of any one of the present invention, or the isolated antibody or functional fragment thereof of the present invention, and/or to a nucleic acid sequence or nucleic acid sequences obtainable by the method according to the ninth aspect of the present invention.

In a fifth aspect, the present invention relates to a vector or a collection of vectors comprising the nucleic acid sequence or a collection of nucleic acid sequences of the present invention.

In a sixth aspect, the present invention relates to a host cell, particularly an expression host cell, comprising the nucleic acid sequence or the collection of nucleic acid sequences of the present invention, or the vector or collection of vectors of the present invention.

In a seventh aspect, the present invention relates to a method for producing the antibody VL domain of any one of the present invention, or the isolated antibody or functional fragment thereof of the present invention, comprising the step of expressing the nucleic acid sequence or the collection of nucleic acid sequences of the present invention, or the vector or collection of vectors of the present invention, or the host cell, particularly an expression host cell, of the present invention.

In an eighth aspect, the present invention relates to a method for generating a humanized rabbit antibody or rodent antibody, particularly a mouse or rat antibody, comprising the steps of:
  a) immunization of rabbits or rodents, particularly mice or rats, with an antigen of interest;
  b) isolating at least one antibody of interest; and
  c) cloning of the VL CDR regions of said at least one antibody of interest into a nucleic acid sequence encoding an antibody VL domain according to the present invention.

In a particular embodiment, the framework region IV in said antibody VL domain is not FGQGTKLTVLG (SEQ ID No. 15), when generating a humanized rabbit antibody.

In particular embodiments, the method of the present invention further comprises one or more of the steps of:
  aa. clonal isolation of affinity matured memory B-cells that interact with the antigen of interest, particularly by using fluorescence activated cell-sorting;
  ab. cultivation of single B cells in a co-cultivation system that does not require immortalization of single B cell clones;
  ac. screening of B cell culture supernatants in a cell-based ELISA to identify at least one antibody binding to the antigen of interest; and/or
  ad. cloning of the VH CDR regions of at least one antibody into a nucleic acid sequence encoding a human antibody VH domain.

Methods for the humanization of rabbit antibodies or rodent antibodies are well known to anyone of ordinary skill in the art (see, for example, Borras, loc. cit.; Rader et al, The FASEB Journal, express article 10.1096/fj.02-0281fje, published online Oct. 18, 2002; Yu et al (2010) A Humanized Anti-VEGF Rabbit Monoclonal Antibody Inhibits Angiogenesis and Blocks Tumor Growth in Xenograft Models. PLoS ONE 5(2): e9072. doi:10.1371/journal.pone.0009072). The immunization of the rabbits or rodents may be performed with the antigen of interest as such, such as a protein, or, in the case of peptide or protein antigens, by DNA immunization of a rabbit with a nucleic acid, e.g. a plasmid, encoding the peptides or proteins of interest.

In a ninth aspect, the present invention relates to a method for generating a nucleic acid sequence encoding an antibody VL domain according to the present invention, or one or more nucleic acid sequences encoding an isolated antibody or functional fragment thereof according to the present invention, comprising combining in one or more steps nucleic acid sequences encoding (i) human Vκ framework regions I to III; (ii) CDR domains CDR1, CDR2 and CDR3, and (iii) a framework region IV, which is selected from
  a. a human Vλ germ line sequence for framework region IV, particularly a Vλ germ line sequence selected from the list of: SEQ ID NO. 16 to 22;
  b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and
  c. a Vλ-based sequence, which has one or two mutations, particularly one mutation, compared to the closest human Vλ germ line sequence for framework region IV;

particularly using one of the following methods:
i. replacing in a nucleic acid construct, particularly in a recombinant vector, comprising a nucleic acid sequence encoding a human or humanized Vκ domain the Vκ framework region IV by a framework region IV, which is selected from
  a. a human Vλ germ line sequence for framework region IV, particularly a Vλ germ line sequence selected from the list of: SEQ ID NO. 16 to 22;
  b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and
  c. a Vλ-based sequence, which has one or two mutations, particularly one mutation, compared to the closest human Vλ germ line sequence for framework region IV;
ii. inserting in one or more steps into a nucleic acid construct, particularly into a recombinant vector, comprising a nucleic acid sequence encoding a framework region IV one or more nucleic acid sequences encoding (i) human Vκ framework regions I to III; and (ii) CDR domains CDR1, CDR2 and CDR3, wherein said framework region IV is selected from
  a. a human Vλ germ line sequence for framework region IV, particularly a Vλ germ line sequence selected from the list of: SEQ ID NO. 16 to 22;
  b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and
  c. a Vλ-based sequence, which has one or two mutations, particularly one mutation, compared to the closest human Vλ germ line sequence for framework region IV;
iii. mutating in a nucleic acid sequence encoding a human or humanized Vκ domain the nucleic acid sequence encoding framework region IV to generate a framework region IV, which is selected from
  a. a human Vλ germ line sequence for framework region IV, particularly a Vλ germ line sequence selected from the list of: SEQ ID NO. 16 to 22;
  b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and
  c. a Vλ-based sequence, which has one or two mutations, particularly one mutation, compared to the closest human Vλ germ line sequence for framework region IV; or
iv. replacing in one or more steps in a nucleic acid construct, particularly in a recombinant vector, comprising a nucleic acid sequence encoding a light chain domain comprising human Vκ framework regions I to III, CDR domains CDR1, CDR2 and CDR3, and a framework region IV, one or more of the nucleic acid sequences encoding said CDR domains by nucleic acid sequence(s) encoding the corresponding CDR domain(s) from an antibody of interest, wherein said framework region IV is selected from a. a human Vλ germ line sequence for framework region IV, particularly a Vλ germ line sequence selected from the list of: SEQ ID NO. 16 to 22;

b. a Vλ-based sequence, which is (bi) a consensus Vλ sequence from human Vλ germ line sequences for framework region IV, particularly SEQ ID NO. 17; or (bii) a consensus Vλ sequence from rearranged human Vλ sequences for framework region IV, particularly a Vλ consensus sequence selected from the list of: SEQ ID NO. 16 and 17; and c. a Vλ-based sequence, which has one or two mutations, particularly one mutation, compared to the closest human Vλ germ line sequence for framework region IV;

In particular embodiments of the methods of the present invention, wherein in the case of (b) or (c) framework region IV has the sequence FGQGTKLTVLG (SEQ ID No. 15)

(w) said human Vκ framework regions I to III are different from the framework regions as found in the list of clones: FW1.4gen (SEQ ID NO: 4), 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, and 43-FW1.4opt;

(x) said human Vκ framework regions I to III are different from a sequence obtainable by permutation from the sequences of the framework regions as found in the list of clones: FW1.4gen (SEQ ID NO: 4), 375-FW1.4opt, 435-FW1.4opt, 509-FW1.4opt, 511-FW1.4opt, 534-FW1.4opt, 567-FW1.4opt, 578-FW1.4opt, 1-FW1.4opt, 8-FW1.4opt, 15-FW1.4opt, 19-FW1.4opt, 34-FW1.4opt, 35-FW1.4opt, 42-FW1.4opt, and 43-FW1.4opt;

(y) said human Vκ framework regions I to III are different from a sequence obtainable by mutation of the sequence FW1.4gen (SEQ ID NO: 4) at one or more of positions 15, 22, 48, 57, 74, 87, 88, 90, 92, 95, 97 and 99 (AHo numbering); or (z) said human Vκ framework regions I to III comprise not more than five mutations compared to the respective regions in the human Vκ sequence with SEQ ID No: 8, particularly less than five, less than four, less than three, particularly only one or no mutation compared to the human Vκ sequence with SEQ ID No: 8.

In a particular embodiment, said framework region IV is not FGQGTKLTVLG (SEQ ID No. 15), when one or more of said CDR domain(s) are of rabbit origin.

EXAMPLES

The following examples illustrate the invention without limiting its scope.

Example 1: Construction of scFv Constructs with Exemplary Rabbit CDRs

It was our aim to identify variable domains that show improved stability with respect to unfolding and aggregation tendency. In addition, these domains should be as close as possible to the human germ line repertoire to minimize the risk eliciting an immune response in human beings. Surprisingly we found that the combination of a VH3 consensus framework with a chimeric VL domain composed of framework regions I to III from a consensus Vκ1 and the framework region IV (see FIG. 1) from different Vλ domains resulted in a scFv construct of superior biophysical properties.

Starting point for our invention was the human VH3 and Vκ1 consensus framework Hu-4D5 as it was published already in 1992 (Carter, loc. cit.). We engrafted the CDRs of an exemplary rabbit anti-TNFα antibody (WO/2009/155723) onto the hu-4D5 variable domains as described (Rader 2000, loc. cit.; WO 2005/016950; WO 2008/004834). The humanized variable domains were linked by a flexible peptide linker as described by Borras, loc. cit, resulting in a single-chain Fv (scFv) fragment (scFv1).

In addition to hu-4D5, another published framework solution was tested, namely the framework FW1.4gen (scFv2), of which extensive biophysical data is published (Borras, loc. cit.). The framework FW1.4gen includes several amino acid substitutions when compared to hu-4D5 thus deviating from the human consensus. In the VH, such differences probably result from affinity maturation, on one hand because it originates from a human cDNA library, containing sequences of mature antibodies that have undergone somatic hypermutation, rather than germline sequences, and on the other hand because several mutations have been introduced by the authors for purpose of accommodating rabbit CDRs. In the VL no or only few mutations have been deliberately introduced, suggesting that most differences result from the germ line sequence used somatic hypermutation or possibly are artifacts resulting from library cloning procedures.

Experimental determination of the thermal unfolding of the two constructs based either on hu-4D5 or FW1.4gen (scFv1 and scFv2, respectively) showed a superior performance of scFv1, the framework with higher homology to the human consensus sequence, thus being in line with the literature. Surprisingly this superior stability did not convert into a higher stability with respect to monodispersity during storage under stress conditions (see Table 4). On the contrary, scFv2 showed better stability here.

Figure 3:
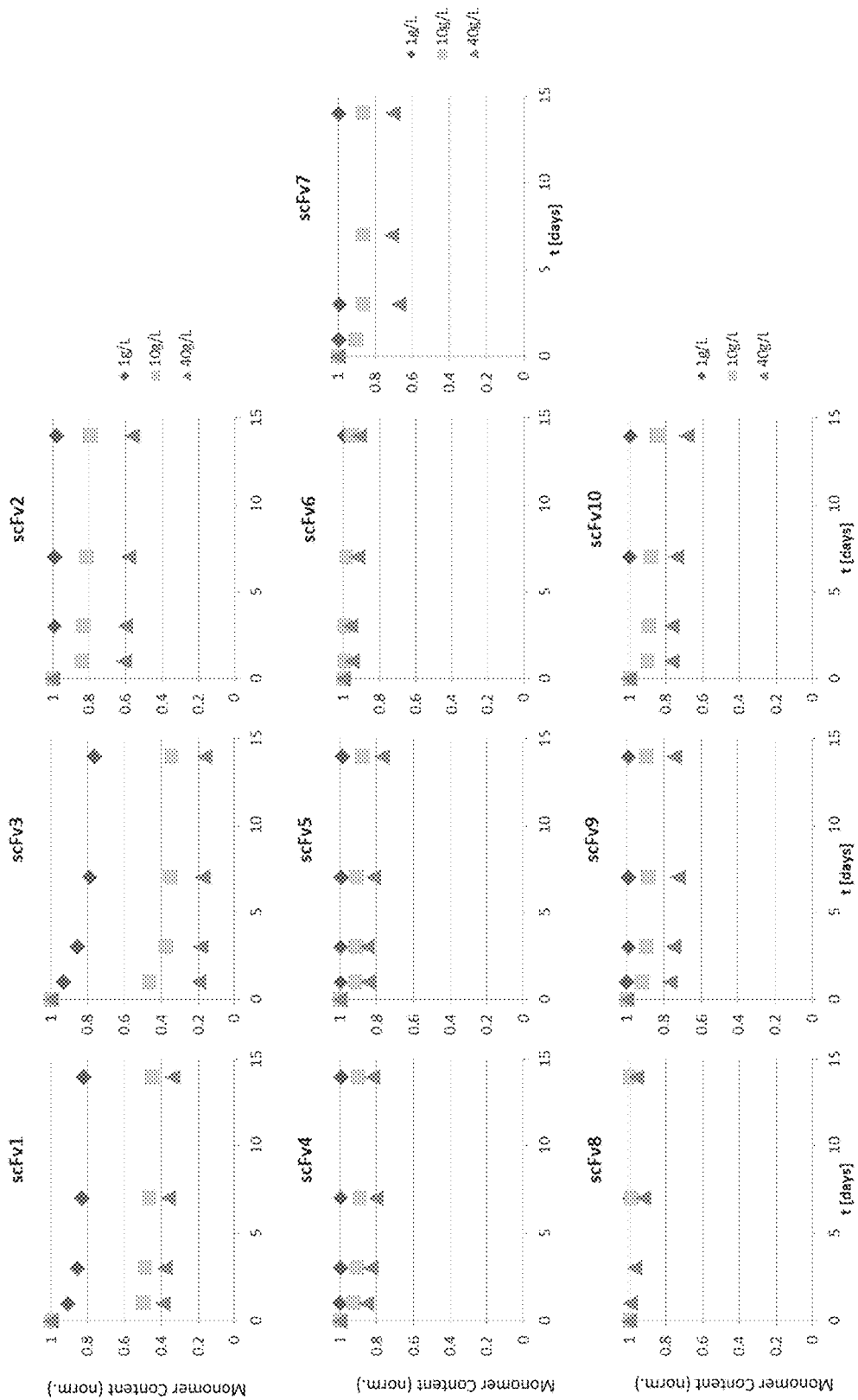
FIG. 3 shows a comparison of the normalized time-resolved loss of monomer content for scFv1 to scFv10.

In an attempt to rationalize the observed differences in stability the sequence variation in the frameworks were more closely examined. A stretch of five amino acids in the framework IV region was identified that led to impaired stability of the monomeric state in the stress stability study when converted to the consensus sequence of Vκ1 in FW1.4gen (scFv3) (see (FIG. 3).

This finding was highly unexpected since it contradicts the common understanding that the consensus sequence, in this case of Vκ1, would present the most favored solution with regard to the stability of the respective variable domain. Based on this discovery we set out to further examine the determinants of domain stability in the model system. As the five amino acids in framework region IV of FW1.4 made the joining segment (framework region IV) resembling a A-type framework region IV sequence rather than a K-type, we hypothesized that A-type joining segments may be favorable over K-type joining segments for the stability of the Vκ1-VH3 variable domains.

Indeed we found that the full replacement of Vκ1 framework region IV by the corresponding Vλ framework region (scFv5, scFv9) led to favorable stability profiles compared to scFv1 or scFv2 in terms of both the midpoint of thermal unfolding (Table 3) and the stability of the monomeric state during the stress stability study (Table 4). Furthermore, the introduction of different truncated Vλ framework region IV germline motifs into the background of the Vκ1 consensus framework (scFv7, scFv10) showed some stabilizing effects. Importantly, full replacement of Vκ1 framework region IV by a Vλ region IV has a lower potential to be immunogenic as all individual framework regions remain identical to germline or to germline consensus with this approach.

In addition, position AHo101 in framework III was identified by comparing structural models of Vκ and Vλ variable domains to be contributing to the packing of framework region IV (FIG. 4). The introduction of a Vλ consensus residue at this position (scFv4, scFv6, scFv8) led to a further increase of the domain stability in thermal unfolding (Table 3) and stress stability (Table 4).

In summary, it has been found that in the context of scFv variable domain constructs, a superior stability profile is achieved by combining consensus framework regions IV from different Vλ germline genes with the framework regions I to III of a Vκ sequence. The stability of these artificial and chimeric variable domains is further improved by the modification F101E (according to the AHo numbering scheme) in framework region III of the variable light domain, a position that is in close spatial proximity to framework region IV.

Importantly, based on published cases (Schafer, Protein Engineering, Design & Selection 25 (2012) 485-505) it is expected that the preferred properties of the variable domains translate into other antibody formats as well.

An exemplary rabbit binder was identified from the literature (WO 2009/155723) and its CDRs were grafted onto the respective variable domains of a human consensus VH3/Vκ1 framework (Rader 2000, loc. cit.; WO/2005/016950; WO 2008/004834; U.S. Pat. No. 8,293,235), using the CDR definitions as published in Borras et al (Borras, loc. cit.). For the loop grafting of the rabbit CDRs the sequence stretches CDR-L1 (L24-L42), CDR-L2 (L58-L72), CDR-L3 (L107-L138), CDR-H1 (H27-H42), CDR-H2 (H57-H76), CDR-H3 (H109-H138) according to the numbering by Honegger (Honegger & Plückthun, loc. cit.; see FIG. 2) were transferred onto the human frameworks. Based on these humanized variable domains the scFv constructs were generated by connecting the VL and VH by a flexible Gly4-Ser linker, thus resulting in a configuration of NH$_2$—VL-linker-VH—COOH.

Methods

Construct Design and Manufacture

The resulting amino acid sequence was de novo synthesized and cloned into an adapted expression vector for *E. coli* expression that is based on a pET26b(+) backbone (Novagen). The expression construct was transformed into the *E. coli* strain BL12 (DE3) (Novagen) and the cells were cultivated in 2YT medium (Sambrook, J., et al., Molecular Cloning: A Laboratory Manual) as a starting culture. Expression cultures were inoculated and incubated in baffled flasks at 37° C. and 200 rpm. Once the OD600 nm of 1 was reached protein expression was induced by the addition of IPTG at a final concentration of 0.5 mM. After overnight expression the cells were harvested by centrifugation at 4000 g. For the preparation of inclusion bodies the cell pellet was resuspended in IB Resuspension Buffer (50 mM Tris-HCl pH 7.5, 100 mM NaCl, 5 mM EDTA, 0.5% TRITON™ X-100 (e.g., a non-ionic surfactant)). The cell slurry was supplemented with 1 mM DTT, 0.1 mg/mL Lysozyme, 10 mM Leupeptin, 100 μM PMSF and 1 μM Pepstatin. Cells were lysed by 3 cycles of ultrasonic homogenization while being cooled on ice. Subsequently 0.01 mg/mL DNAse was added and the homogenate was incubated at room temperature for 20 min. The inclusion bodies were sedimented by centrifugation at 10,000 g and 4° C. The IBs were resuspended in IB Resuspension Buffer and homogenized by sonication before another centrifugation. In total a minimum of 3 washing steps with IB Resuspension Buffer were performed and subsequently 2 washes with IB Wash Buffer were performed to yield the final IBs.

For protein refolding the isolated IBs were resuspended in Solubilization Buffer (100 mM Tris/HCl pH 8.0, 6 M Gdn-HCl, 2 mM EDTA) in a ratio of 5 mL per g of wet IBs. The solubilization was incubated for 30 min at room temperature until DTT was added at a final concentration of 20 mM and the incubation was continued for another 30 min. After the solubilization is completed the solution is cleared by 10 min centrifugation at 8500 g and 4° C. The refolding is performed by rapid dilution at a final protein concentration of 0.5 g/L of the solubilized protein in Refolding Buffer (typically: 100 mM Tris-HCl pH 8.0, 4.0 M Urea, 5 mM Cysteine, 1 mM Cystine). The refolding reaction is routinely incubated for a minimum of 14 h. The resulting protein solution is concentrated and buffer exchanged by diafiltration into Native Buffer (50 mM Citrate-Phosphate pH 6.4, 200 mM NaCl). The refolded protein is purified by size-exclusion chromatography on a suitable resin material (e.g. Superdex 75, GE Healthcare). The isolated monomer fraction is analyzed by size-exclusion HPLC, SDS-PAGE for purity and UV/Vis spectroscopy for protein content. The protein concentration is adjusted to the required levels and the stability analysis is performed.

Comparison of Structural Models

The three-dimensional structures of variable domains VL Kappa and VL Lambda were compared using the example of structural models available in the PDB (PDB ID 1 FVC and PDB ID 2A9M, respectively). The analysis of the packing of the VL framework region IV revealed differences in the side-chain orientation from position 147 onwards. In addition the orientation of the amino acid side chain at position 101 differed in the Vκ and Vλ structures. As illustrated by FIG. 4 the different packing of the central amino acid (position 101) is apparent. In the case of the Vκ the phenylalanine 101 points in the core of the domain, in the lambda variable domain, however, the glutamate at position 101 is solvent exposed and the V147 (arrow) is in turn positioned into the hydrophobic core. Based on this observation variable domains containing the amino acid exchange F101E were generated (SEQ ID No: 8, 11 and 13) to accommodate the Vλ specific packing of the Vλ framework IV.

Example 2: Determination of Biophysical Data for scFv Constructs

Thermal Unfolding

The midpoint of transition for the thermal unfolding of the tested constructs was determined by Differential Scanning Fluorimetry (DSF), essentially as described by Niesen (Niesen et al., Nat Protoc. 2 (2007) 2212-21). The DSF assay is performed in a qPCR machine (e.g. MX3005p, Agilent Technologies). The samples were diluted in buffer (citrate-phosphate pH 6.4, 0.25 M NaCl) containing a final concentration of 5×SYPRO orange in a total volume of 25 μL. In a buffer scouting experiment the pH dependence of the unfolding temperature was determined and comparable pH characteristics was observed for all constructs. Samples were measured in triplicates and a temperature ramp from 25-96° C. programmed. The fluorescence signal was acquired and the raw data was analyzed with the GraphPad Prism (GraphPad Software Inc.).

Stress Stability Study

The protein was analyzed over the course of two weeks and storage at 37° C. with respect to oligomerization by size-exclusion high-performance liquid chromatography (SE-HPLC) and degradation by sodium dodecyl sulfate polyacrylamide gel electrophoresis (SDS-PAGE). Prior to the study the samples were concentrated to 1, 10 and 40 g/L and t0 time points were determined. The monomer content was quantified by separation of the samples on a Shodex KW-402.5-4F (Showa Denko) and evaluation of the resulting chromatograms. For the calculation of the relative percentage of protein monomer the area of the monomeric peak was divided by the total area of peaks that could not be attributed to the sample matrix. The protein degradation was assessed by SDS-PAGE analysis with Any kD Mini-Protean TGX gels (Bio-Rad Laboratories) and stained with Coomassie brilliant blue. The protein concentration was monitored at the different time points by UV-Vis spectroscopy with an Infinity reader M200 Pro equipped with Nanoquant plate (Tecan Group Ltd.).

Figure 5:
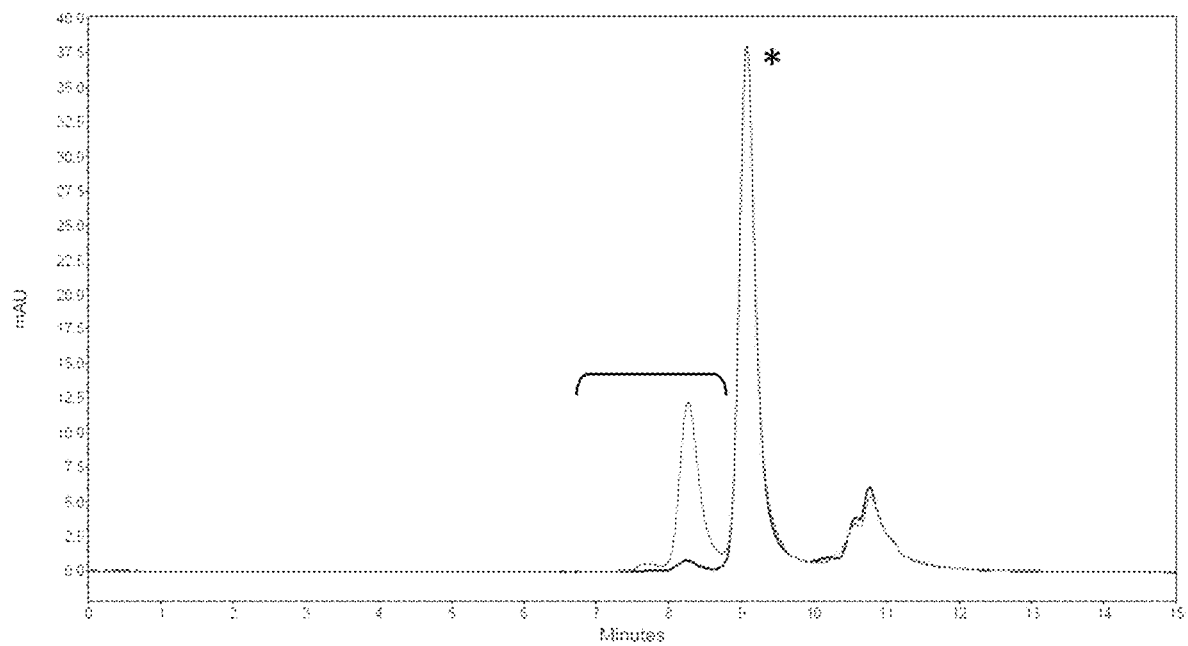
FIG. 5 shows an overlay of the normalized SE-HPLC chromatograms of two scFv constructs of a humanized mouse monoclonal antibody with the native/original variable domains (grey) and a with the VL domain containing a lambda framework IV (black). The normalized scFv monomer peak is annotated with an asterisk (*), while the oligomer and aggregate peaks are highlighted with a bracket.

Example 3: Construction of scFv Constructs from a Marketed Humanized Mouse Monoclonal Antibody To confirm the broad applicability of the proposed concept for the stabilization of antibody variable domains, two single-chain Fv constructs were generated based on a marketed humanized mouse monoclonal antibody comprising a Vkappa light chain. For the first construct the original variable domain sequences were used as published for the amino acid sequence of the IgG, whereas for the second construct a modified sequence was used where the framework region IV of the variable light chain domain was replaced by the respective sequence from a lambda germline gene. In the scFv constructs the variable domains were linked by a 20 amino acid flexible (Gly$_4$Ser)$_4$ linker (SEQ ID NO: 1), thus resulting in a configuration of NH$_2$—VL-linker-VH—COOH as used in model constructs scFv1 to scFv10 (see Table 2). The expression and refolding of the scFv molecules were performed as described above, and the refolded proteins were purified by affinity chromatography over protein L resin. Analysis of the purified proteins by SE-HPLC revealed marked differences in the producibility of the constructs that manifested in a significantly improved monomer content of the construct containing the lambda framework IV in the VL (see FIG. 5). In addition the thermal unfolding analysis of the construct with the original sequence and the molecule containing the lambda framework IV in the VL resulted in a midpoint of unfolding of 69.9 and 71.2° C., respectively. This observation is in line with the results described in Section [0082].

Example 4: Construction of scFv Constructs with a Shorter Linker Sequence

In order to analyze the impact of the linker sequence, alternative constructs were made in the same way as described above in Example 1 using a shorter 15 amino acid (Gly$_4$Ser)$_3$ linker (SEQ ID NO: 34), Except for the linker, the two constructs, scFv11 and scFv12, correspond to constructs scFv1 and scFv5, respectively (see Table 2). A stress-stability study was performed as described above in Example 2. As shown in Table 4, the construct scFv12 with the shorter linker containing the lambda framework IV in the VL showed an increased stability relative to the construct with the consensus kappa light chain scFv11. The overall stability of the molecules was lower than the corresponding constructs with the longer linker. It is well known that scFv stability is increased by using 20mer or 25mer linkers instead of 15mer linkers (see Worn and Plückthun, J. Mol. Biol. 305 (2001) 989-1010). Thus these findings are in line with results with 20mer linkers and confirm that the stability of a variable domain is improved by introducing a lambda framework IV in the VL.

TABLE 1

List of protein sequences

| SEQ ID NO: | Type | Sequence |
| --- | --- | --- |
| 1 | Linker | GGGGSGGGGSGGGGSGGGGS |
| 2 | VL | DIQMTQSPSSLSASVGDRVTITCQASQSISDWLAWYQQK PGKAPKLLIYGASRLASGVPSRFSGSRSGTDFTLTISSLQP EDFATYYCQQGWSDSYVDNLFGQGTKVEIKR |
| 3 | VH | EVQLVESGGGLVQPGGSLRLSCAVSGFSLSSGAMSWVR QAPGKGLEWIGVIISSGATYYASWAKGRFTISKDNSKNTV YLQMNSLRAEDTAVYYCARGGPDDSNSMGTFDPWGQGT LVTVSS |
| 4 | VL | EIVMTQSPSTLSASVGDRVIITCQASQSISDWLAWYQQKP GKAPKLLIYGASRLASGVPSRFSGSGSGAEFTLTISSLQPD DFATYYCQQGWSDSYVDNLFGQGTKLTVLG |
| 5 | VH | EVQLVESGGGLVQPGGSLRLSCTVSGFSLSSGAMSWVR QAPGKGLEWVGVIISSGATYYASWAKGRFTISKDTSKNTV YLQMNSLRAEDTAVYYCARGGPDDSNSMGTFDPWGQGT LVTVSS |
| 6 | VL | EIVMTQSPSTLSASVGDRVIITCQASQSISDWLAWYQQKP GKAPKLLIYGASRLASGVPSRFSGSGSGAEFTLTISSLQPD DFATYYCQQGWSDSYVDNLFGQGTKVEIKR |
| 7 | VL | DIQMTQSPSSLSASVGDRVTITCQASQSISDWLAWYQQK PGKAPKLLIYGASRLASGVPSRFSGSGSGTDFTLTISSLQP EDFATYYCQQGWSDSYVDNLFGQGTKLTVLG |

TABLE 1-continued

List of protein sequences

| SEQ ID NO: | Type | Sequence |
|---|---|---|
| 8 | VL | DIQMTQSPSSLSASVGDRVTITCQASQSISDWLAWYQQK PGKAPKLLIYGASRLASGVPSRFSGSGSGTDFTLTISSLQP EDEATYYCQQGWSDSYVDNLFGQGTKLTVLG |
| 9 | VL | DIQMTQSPSSLSASVGDRVTITCQASQSISDWLAWYQQK PGKAPKLLIYGASRLASGVPSRFSGSGSGTDFTLTISSLQP EDFATYYCQQGWSDSYVDNLFGGGTKLTVLG |
| 10 | VL | DIQMTQSPSSLSASVGDRVTITCQASQSISDWLAWYQQK PGKAPKLLIYGASRLASGVPSRFSGSGSGTDFTLTISSLQP EDFATYYCQQGWSDSYVDNLFGQGTKVTVLG |
| 11 | VL | DIQMTQSPSSLSASVGDRVTITCQASQSISDWLAWYQQK PGKAPKLLIYGASRLASGVPSRFSGSGSGTDFTLTISSLQP EDEATYYCQQGWSDSYVDNLFGGGTKLTVLG |
| 12 | VL | DIQMTQSPSSLSASVGDRVTITCQASQSISDWLAWYQQK PGKAPKLLIYGASRLASGVPSRFSGSGSGTDFTLTISSLQP EDFATYYCQQGWSDSYVDNLFGTGTKVTVLG |
| 13 | VL | DIQMTQSPSSLSASVGDRVTITCQASQSISDWLAWYQQK PGKAPKLLIYGASRLASGVPSRFSGSGSGTDFTLTISSLQP EDEATYYCQQGWSDSYVDNLFGTGTKVTVLG |
| 14 | VH | EVQLVESGGGLVQPGGSLRLSCAASGFSLSSGAMSWVR QAPGKGLEWIGVIISSGATYYASWAKGRFTISRDNSKNTV YLQMNSLRAEDTAVYYCARGGPDDSNSMGTFDPWGQGT LVTVSS |
| 15 | 1.4gen framework region IV | FGQGTKLTVLG |
| 16 | FR_IV Vλ germ line | FGTGTKVTVLG |
| 17 | FR_IV Vλ germ line | FGGGTKLTVLG |
| 18 | FR_IV Vλ germ line | FGGGTQLIILG |
| 19 | FR_IV Vλ germ line | FGEGTELTVLG |
| 20 | FR_IV Vλ germ line | FGSGTKVTVLG |
| 21 | FR_IV Vλ germ line | FGGGTQLTVLG |
| 22 | FR_IV Vλ germ line | FGGGTQLTALG |
| 23 | Vk1 consensus (rearranged) | DIQMTQSPSSLSASVGDRVTITCRASQSISNYLNWYQQKP GKAPKLLIYAASSLQSGVPSRFSGSGSGTDFTLTISSLQPE DFATYYCQQYYSTPLTFGQGTKVEIKR |
| 24 | Vk2 consensus (rearranged) | DIVMTQSPLSLPVTPGEPASISCRSSQSLLHSNGYNYLDW YLQKPGQSPQLLIYLGSNRASGVPDRFSGSGSGTDFTLKI SRVEAEDVGVYYCMQALQTPYTFGQGTKLEIKR |
| 25 | Vk3 consensus (rearranged) | EIVLTQSPGTLSLSPGERATLSCRASQSVSSSYLAWYQQK PGQAPRLLIYGASSRATGIPDRFSGSGSGTDFTLTISRLEP EDFAVYYCQQYGNSPYTFGQGTKVEIKR |
| 26 | Vk4 consensus (rearranged) | DIVMTQSPDSLAVSLGERATINCKSSQSVLYSSNNKNYLA WYQQKPGQPPKLLIYWASTRESGVPDRFSGSGSGTDFTL TISSLQAEDVAVYYCQQYYSTPPTFGQGTKVEIKR |
| 27 | VH1A consensus (rearranged) | QVQLVQSGAEVKKPGSSVKVSCKASGGTFSSYAISWVRQ APGQGLEWMGGIIPIFGTANYAQKFQGRVTITADESTSTA YMELSSLRSEDTAVYYCARAPGYCSGFDYWGQGTLVTVS S |

TABLE 1-continued

List of protein sequences

| SEQ ID NO: | Type | Sequence |
|---|---|---|
| 28 | VH1B consensus (rearranged) | QVQLVQSGAEVKKPGASVKVSCKASGYTFTSYYMHWVR QAPGQGLEWMGWINPNSGNTNYAQKFQGRVTMTRDTSI STAYMELSSLRSDDTAVYYCARDGDGGFDYWGQGTLVT VSS |
| 29 | VH2 consensus (rearranged) | QVTLKESGPALVKPTQTLTLTCTFSGFSLSTSGMGVSWIR QPPGKALEWLAHIDWDDDKYYSTSLKSRLTISKDTSKNQV VLTMTNMDPVDTATYYCARIHNIGEAFDVWGQGTLVTVSS |
| 30 | VH3 consensus (rearranged) | EVQLVESGGGLVQPGGSLRLSCAASGFTFSSYAMHWVR QAPGKGLEWVSVISYDGGNTYYADSVKGRFTISRDNSKN TLYLQMNSLRAEDTAVYYCARDRGGSGDYWGQGTLVTV SS |
| 31 | VH4 consensus (rearranged) | QVQLQESGPGLVKPSETLSLTCTVSGGSISSYYWSWIRQP PGKGLEWIGEIYHSGSTNYNPSLKSRVTISVDTSKNQFSL KLSSVTAADTAVYYCARGRGGGGVFDYWGQGTLVTVSS |
| 32 | VH5 consensus (rearranged) | EVQLVQSGAEVKKPGESLKISCKGSGYSFTSYWIGWVRQ MPGKGLEWMGIIYPGDSDTRYSPSFQGQVTISADKSISTA YLQWSSLKASDTAMYYCARLGGGGYYFDYWGQGTLVTV SS |
| 33 | VH6 consensus (rearranged) | QVQLQQSGPGLVKPSQTLSLTCAISGDSVSSNSAAWNWI RQSPSRGLEWLGRTYYRSKWYNDYAVSVKSRITINPDTS KNQFSLQLNSVTPEDTAVYYCARDPGGFDVWGQGTLVTV SS |
| 42 | Linker | GGGGSGGGGSGGGGS |

(in SEQ ID NOs: 23 to 33, the CDR regions are indicated in bold and italic letters)

TABLE 2

Combinations of variable domains for the different scFv constructs

| scFv construct | Variable domain 1 | Linker | Variable domain 2 |
|---|---|---|---|
| scFv1 | SEQ ID 2 | SEQ ID 1 | SEQ ID 3 |
| scFv2 | SEQ ID 4 | SEQ ID 1 | SEQ ID 5 |
| scFv3 | SEQ ID 6 | SEQ ID 1 | SEQ ID 3 |
| scFv4 | SEQ ID 11 | SEQ ID 1 | SEQ ID 14 |
| scFv5 | SEQ ID 9 | SEQ ID 1 | SEQ ID 14 |
| scFv6 | SEQ ID 8 | SEQ ID 1 | SEQ ID 14 |
| scFv7 | SEQ ID 7 | SEQ ID 1 | SEQ ID 14 |
| scFv8 | SEQ ID 13 | SEQ ID 1 | SEQ ID 14 |
| scFv9 | SEQ ID 12 | SEQ ID 1 | SEQ ID 14 |
| scFv10 | SEQ ID 10 | SEQ ID 1 | SEQ ID 14 |
| scFv11 | SEQ ID 2 | SEQ ID 42 | SEQ ID 3 |
| scFv12 | SEQ ID 9 | SEQ ID 42 | SEQ ID 14 |
| scFv5 | SEQ ID 9 | SEQ ID 1 | SEQ ID 14 |
| scFv6 | SEQ ID 8 | SEQ ID 1 | SEQ ID 14 |
| scFv7 | SEQ ID 7 | SEQ ID 1 | SEQ ID 14 |
| scFv8 | SEQ ID 13 | SEQ ID 1 | SEQ ID 14 |
| scFv9 | SEQ ID 12 | SEQ ID 1 | SEQ ID 14 |
| scFv10 | SEQ ID 10 | SEQ ID 1 | SEQ ID 14 |
| scFv11 | SEQ ID 2 | SEQ ID 42 | SEQ ID 3 |
| scFv12 | SEQ ID 9 | SEQ ID 42 | SEQ ID 14 |

TABLE 3

The midpoint of transition for the thermal unfolding was determined for all constructs by differential scanning fluorimetry

| Construct ID | Tm |
|---|---|
| scFv 1 | 70.19 ± 0.22 |
| scFv 2 | 66.82 ± 0.37 |
| scFv 3 | 65.44 ± 0.15 |
| scFv 4 | 74.31 ± 0.04 |
| scFv 5 | 70.86 ± 0.16 |
| scFv 6 | 75.19 ± 0.13 |
| scFv 7 | 68.42 ± 0.05 |
| scFv 8 | 75.45 ± 0.36 |
| scFv 9 | 71.15 ± 0.27 |
| scFv 10 | 71.25 ± 0.29 |
| scFv 11 | 70.34 ± 0.20 |
| scFv 12 | 70.18 ± 0.03 |

TABLE 4

Monomer loss during storage

| SEQ ID | 1 g/L at 37° C. | 10 g/L at 37° C. | 40 g/L at 37° C. |
|---|---|---|---|
| scFv 1 | −16.8% | −44.3% | −34.7% |
| scFv 2 | −1.9% | −20.1% | −39.6% |
| scFv 3 | −23.0% | −64.7% | −81.0% |
| scFv 4 | −0.9% | −9.2% | −14.0% |
| scFv 5 | −1.6% | −11.4% | −17.0% |
| scFv 6 | −0.8% | −4.0% | −6.5% |
| scFv 7 | −0.6% | −13.1% | −25.4% |
| scFv 8 | 0.1% | −0.2% | −3.1% |
| scFv 9 | −1.3% | −10.1% | −22.9% |
| scFv 10 | −0.5% | −14.4% | −26.7% |
| scFv 11 | −56.3% | −77.7% | −80.2% |
| scFv 12 | −5.7% | −41.3% | −65.9% |

NOTE:
entries in italics are from scFv constructs with Vκ-type framework IV regions

TABLE 5

List of clones listed in Borras et al. (loc. cit.) and sequence variations
All clones listed below have the sequence of FW1.4gen (SEQ ID NO: 4), but differ in the positions indicated below in bold letters (numbering of positions according to Borras et al. (loc. cit.))

| | VL position | | | | | | | | | | | |
|---|---|---|---|---|---|---|---|---|---|---|---|---|
| | 15 | 22 | 40 | 49 | 58 | 69 | 70 | 72 | 74 | 77 | 79 | 81 |
| FW1.4gen (SEQ ID NO: 4) | V | T | P | Y | V | A | E | T | T | S | Q | D |
| 375-FW1.4opt | V | T | P | Y | V | T | Q | T | T | S | Q | D |
| 435-FW1.4opt | V | K | P | Y | V | A | E | T | T | S | Q | D |
| 509-FW1.4opt | V | T | P | Y | V | T | E | T | T | S | Q | D |
| 511-FW1.4opt | V | T | P | Y | V | T | E | T | T | S | Q | D |
| 534-FW1.4opt | V | T | P | Y | V | T | E | T | T | S | Q | D |
| 567-FW1.4opt | V | T | P | Y | V | T | Q | T | T | S | Q | D |
| 578-FW1.4opt | V | T | P | Y | V | T | Q | T | T | S | Q | D |
| 1-FW1.4opt | V | T | P | Y | V | T | E | T | T | S | Q | D |
| 8-FW1.4opt | V | T | P | Y | V | T | D | T | A | S | Q | D |
| 15-FW1.4opt | V | T | P | Y | V | T | E | T | T | S | Q | D |
| 19-FW1.4opt | V | T | P | Y | V | T | Q | T | T | S | Q | D |
| 34-FW1.4opt | L | T | S | Y | V | A | E | S | T | S | Q | D |
| 35-FW1.4opt | V | T | P | Y | V | T | E | T | T | S | Q | D |
| 42-FW1.4opt | V | T | P | Y | V | T | E | T | T | S | Q | D |
| 43-FW1.4opt | V | K | P | Y | F | A | E | T | T | G | E | A |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The invention claimed is:

1. An isolated antibody or functional fragment thereof comprising (a) a human VH domain comprising framework regions I to III belonging to a human VH domain subfamily selected from the group consisting of VH1A according to SEQ ID NO: 27, VH1B according to SEQ ID NO: 28, VH2 according to SEQ ID NO: 29, VH3 according to SEQ ID NO: 30, VH4 according to SEQ ID NO: 31, VH5 according to SEQ ID NO: 32, and VH6 according to SEQ ID NO: 33, further comprising a human framework region IV, and (b) a VL domain comprising (i) human Vκ framework regions I to III, wherein said Vκ framework regions I to III belong to a Vκ domain subfamily selected from the group consisting of Vκ1 according to SEQ ID NO: 23, Vκ2 according to SEQ ID NO: 24, Vκ3 according to SEQ ID NO: 25, and Vκ4 according to SEQ ID NO: 26; (ii) VL rabbit or rodent CDR domains CDR1, CDR2 and CDR3; and (iii) a framework region IV, which is a human Vλ germ line sequence for framework region IV selected from the group of sequences consisting of SEQ ID NOs: 16 to 22.

2. The isolated antibody or functional fragment thereof of claim 1, which is selected from the group consisting of: an IgG antibody, a Fab fragment, an scFv fragment, a single-chain diabody, a tandem single-chain diabody, a linear dimeric single-chain diabody, a circular dimeric single-chain diabody, a bispecific T-cell engager, a tandem tri-scFv, a tribody, a triabody, a bispecific Fab2, a di-miniantibody, a tetrabody, an scFv-Fc-scFv fusion, a di-diabody, a DVD-Ig, an IgG-scFab, an scFab-dsscFv, an Fv2-Fc, an IgG-scFv fusion, a bsAb with an scFv linked to the C-terminus of the light chain of an IgG, a Bs1Ab with an scFv linked to the N-terminus of the light chain of an IgG, a Bs2Ab with an scFv linked to N-terminus of the heavy chain of an IgG, a Bs3Ab with an scFv linked to the C-terminus of the heavy chain of an IgG, a Ts1Ab with an scFv linked to the N-terminus of both the heavy chain and the light chain of an IgG, a Ts2Ab with a dsscFv linked to the C-terminus of the heavy chain of an IgG, a Knobs-into-Holes bispecific IgG and a DuoBody bispecific IgG.

3. A pharmaceutical composition comprising the isolated antibody or functional fragment thereof of claim 1, and optionally a pharmaceutically acceptable carrier and/or excipient.

4. A method for producing the isolated antibody or functional fragment thereof according to claim 1, comprising the step of expressing a nucleic acid sequence or a collection of nucleic acid sequences encoding said isolated antibody or functional fragment according to claim 1 or a vector or collection of vectors comprising said nucleic acid sequence or said collection of nucleic acid sequences optionally in a host cell.

* * * * *